United States Patent
Joullie et al.

(10) Patent No.: US 7,651,997 B2
(45) Date of Patent: *Jan. 26, 2010

(54) DEOXO-PROLINE-CONTAINING TAMANDARIN AND DIDEMNIN ANALOGS, DEHYDRO-PROLINE-CONTAINING TAMANDARIN AND DIDEMNIN ANALOGS, AND METHODS OF MAKING AND USING THEM

(75) Inventors: Madeleine M. Joullie, Philadelphia, PA (US); Bo Liang, Glenolden, PA (US); Xiaobin Ding, Piscataway, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/455,937

(22) Filed: Jun. 20, 2006

(65) Prior Publication Data

US 2007/0129289 A1 Jun. 7, 2007

Related U.S. Application Data

(63) Continuation of application No. 09/767,080, filed on Jan. 22, 2001, now Pat. No. 7,064,105, which is a continuation-in-part of application No. 09/545,848, filed on Apr. 7, 2000, now Pat. No. 6,509,315.

(51) Int. Cl.
*A61K 38/00* (2006.01)
*A61K 38/12* (2006.01)
*C07K 16/00* (2006.01)

(52) U.S. Cl. .................. 514/10; 514/11; 530/317; 530/322; 530/323; 530/324; 530/402

(58) Field of Classification Search .............. 514/10, 514/11; 530/317, 322, 323, 324, 402
See application file for complete search history.

(56) References Cited

U.S. PATENT DOCUMENTS

| | | | |
|---|---|---|---|
| 4,160,452 A | 7/1979 | Theeuwes | |
| 4,256,108 A | 3/1981 | Theeuwes | |
| 4,265,874 A | 5/1981 | Bonsen et al. | |
| 4,493,796 A | 1/1985 | Rinehart, Jr. | |
| 4,782,135 A | 11/1988 | Rinehart, Jr. | |
| 5,137,870 A | 8/1992 | Rinehart | |
| 5,504,189 A | 4/1996 | Emling et al. | |
| 7,064,105 B2* | 6/2006 | Joullie et al. ............ | 514/10 |
| 7,122,519 B2 | 10/2006 | Joullié et al. | |
| 2003/0104991 A1 | 6/2003 | Joullié et al. | |
| 2007/0111928 A1 | 5/2007 | Joullié et al. | |
| 2007/0149446 A1 | 6/2007 | Joullié et al. | |

FOREIGN PATENT DOCUMENTS

| | | |
|---|---|---|
| ES | 2 102 322 A1 | 7/1997 |
| WO | WO 98/17275 A1 | 4/1998 |
| WO | WO 98/17302 A1 | 4/1998 |
| WO | WO 02/02596 A2 | 1/2002 |

OTHER PUBLICATIONS

Li et al., Total synthesis and structural investigations of didemnins A, B, and C, J. Am. Chem. Soc., vol. 112, No. 21: Oct. 10, 1990.*
Abdel-Magid et al., 1990, Synlett. 537-539.
Abdel-Magid et al., 1990, Tetrahedron Lett. 31:5595-5598.
Depenbrock et al., 1998, Brit. J. of Cancer 78(6):739-744.
Ewing et al., 1986, Tetrahedron 42:5863-5868.
Ewing et al., 1989, Tetrahedron Lett. 30:3757-3760.
Grubb et al., 1995, Biochem. Biophys, Res. Commun. 215:1130-1136 (Abstract only).
Harris et al., 1987, Tetrahedron Lett. 28:2837-2840.
Harris et al., 1988, Tetrahedron 44:3489-3500.
Johnson et al., 1996, FEBS Lett. 383:1-5.
Johnson et al., 1999, Immunol. Cell. Biol. 77:242-248.
Johnson et al., 1999, J. Cell. Biochem. 72:269-278.
Li et al., 1990, J. Am. Chem. Soc. 112:7659-7672.
Li et al., 1992, Studies in Natural Products Chemistry, 10:241-302.
Liang et al., 1999, Org. Lett. 1:1319-1322.
Mayer et al., 1994, J. Org. Chem. 59:5192-5205.
Mayer et al., 1994, Tetrahedron: Asymmetry 5:519-522.
Pfizenmayer et al., 1998, Bioorg. Med. Chem. Lett., 8:3653-3656 (Abstract only).
Campbell et al., 1998, Brit. J. Of Cancer, 78(6):739-744.
Vervoort, H., et al., "Tamandarins A and B: New Cytotoxic Depsipeptides from a Brazilian Ascidian of the Family Didemnidae," J.Org. Chem. 65:783-792, American Chemical Society (2000).
Joullie, M. M., et al., "Total Synthesis of (−)-Tamandarin B," Tetrahedron Letters 41:9373-9376 Elsevier Science Ltd. (2000).
Liang, B., et al., "Total Synthesis of [(2S)-Hiv$^2$]Didemnin M," J. Org. Chem. 65:4762-4765, American Chemical Society (2000).
Crews, C. M., et al., "Didemnin Binds to the Protein Palmitoyl Thioesterase Responsible for Infantile Neuronal Ceroid Lipofuscinosis," Proc. Natl. Acad. Sci. USA 93:4316-4319 Natl. Acad. Sci. (1996).
Supplementary Partial European Search Report, Application No. EP 01924886.3-2117-US0111607, Jul. 12, 2004.
Ahuja, D., et al., "Inhibition of Protein Synthesis by Didemnins: Cell Potency and SAR," J. Med. Chem. 43:4212-4218, American Chemical Society (Nov. 2000).
Ahuja, D., et al., "Inhibition of Protein Synthesis by Didemnin B: How EF-lα Mediates Inhibition of Translocation," Biochemistry 39:4339-4346, American Chemical Society (Apr. 2000).
Ding, X., et al., "Structure-Activity Relationships of Side-Chain Modified Didemnins," Bioorg. Med. Chem. Lett. 11:231-234, Pergamon Press (Jan. 2001).
Joullié, M.M., et al., "Chemical Defense in Ascidians of the Didemnidae Family," Bioconjugate Chem. 14:30-37, American Chemical Society (Jan.-Feb. 2003).

(Continued)

Primary Examiner—Jon P Weber
Assistant Examiner—Abdel A Mohamed
(74) Attorney, Agent, or Firm—Sterne, Kessler, Goldstein & Fox, P.L.L.C.

(57) ABSTRACT

The present invention relates to tamandarin and didemnin analogs which have a deoxo-proline residue or a dehydro-proline residue in their structure. These analogs are useful as anti-cancer agents and for other purposes. Methods of making these analogs and methods of using them as inhibitors of protein synthesis, cell growth, and tumorigenesis and as enhancers of apoptosis are also provided.

27 Claims, 6 Drawing Sheets

OTHER PUBLICATIONS

Liang, B., et al., "Total Syntheses and Biological Investigations of Tamandarins A and B and Tamandarin A Analogs," *J. Am. Chem. Soc.* 123:4469-4474, American Chemical Society (May 2001).

Mayer, S., et al., "Synthetic Routes to a Constrained Ring Analog of Didemnin B," *J. Org. Chem.* 61:1655-1664, American Chemical Society (1996).

Mayer, S., et al., "The Cyclic Depsipeptide Backbone of the Didemnins," *Acta Cryst.* C51:1609-1614, Blackwell Publishing (1995).

Pfizenmayer, A.J., et al., "Synthesis and Biological Activities of [$N$-MeLeu$^5$] Didemnin B," *Biog. Med. Chem. Lett.* 6:2713-2716, Pergamon Press (1996).

Pfizenmayer, A.J., et al., "Synthesis and Biological Activities of [$N$-MeLeu$^5$]- and [N-MePhe$^5$]- Didemnin B," *Tetrahedron* 55:313-334, Pergamon Press (Jan. 1999).

Portonovo, P., et al., "First Total Synthesis of a Fluorescent Didemnin," *Tetrahedron* 56:3687-3690, Pergamon Press (Jun. 2000).

Ramanjulu, J.M., et al., "Synthetic Studies of a Didemnin B Analog Based on a 2,3-Diamino Sugar Scaffolding," *Journal of the Chinese Chemical Society* 48:1-4, The Chemical Society (Taipei) (2001).

Ramanjulu, J.M., et al., "Syntheses of Acyclic Analogs of Didemnin B," *Synthetic Communications* 27:3259-3272, Marcel Dekker, Inc. (1997).

Ramanjulu, J.M., et al., "Synthesis of a Reduced Ring Analog of Didemnin B," *J. Org. Chem.* 62:4961-4969, American Chemical Society (1997).

Ramanjulu, J.M., et al., "Analogs of the β-Turn of the Cyclodepsipeptide Didemnin B," *Tetrahedron Letters* 37:311-314, Pergamon Press (1996).

Ramanjulu, J.M., et al., "A Facile Synthesis of Benzyl 2-Amino-3-Azido-4-$O$-$p$- Methoxybenzyl-6-$O$-Benzyl-2,3-Dideoxy-α-D-Glucopyranoside: A Key Intermediate in the Formation of a Didemnin B Analog," *J. Carbohydrate Chemistry* 15:371-381, Marcel Dekker, Inc. (1996).

Tarver, J.E., et al., "Total Syntheses of Conformationally Constrained Didemnin B Analogues. Replacements of $N$, $O$-Dimethyltyrosine with L-1,2,3,4-Tetrahydroisoquinoline and L-1,2,3,4-Tetrahydro-7-methoxyisoquinoline," *J. Org. Chem.* 66:7575-7587, American Chemical Society (Nov. 2001).

Vera, M.D., et al., "Synthesis and Biological Evaluation of Didemnin Photoaffinity Analogues," *Biorg. Med. Chem. Lett.* 11:1871-1874, Pergamon Press (Jul. 2001).

Vera, M.D., et al., "Natural Products as Probes of Cell Biology: 20 Years of Didemnin Research," *Medicinal Research Reviews* 22:102-145, John Wiley & Sons, Inc. (Mar. 2002).

Vera, M.D., et al.,"[Lys$^3$] Didemnins as Potential Affinity Ligands," *Biorg. Med. Chem. Lett.* 11:13-16, Pergamon Press (Jan. 2001).

Xiao, D., et al., "Total Synthesis of a Conformationally Constrained Didemnin B," *J. Org. Chem.* 66:2734-2742, American Chemical Society (Apr. 2001).

STNEasy/CAplus English language abstract of document FP1, ES2102322A1, Accession No. 1998:169709.

Jou, G., et al., "Total Synthesis of Dehydrodidemnin B. Use of Uronium and Phosphonium Salt Coupling Reagents in Peptide Synthesis in Solution," *J. Org. Chem.* 62:354-366, American Chemical Society (1997).

Sakai et al., 1996, J. Med. Chem. 39:2819-2834 (American Chemical Society).

Schumacher et al., 1997, Tetrahedron: Asymmetry 9:47-53.

Wipf, 1995, Chem. Rev. 95:2115-2134 (American Chemical Society).

\* cited by examiner a. Me$_2$SO$_4$, KOH, Bu$_4$N$^+$HSO$_4^-$, THF, 78%; b. H$_2$, Pd/C, 99%; c. MeOH, SOCl$_2$ 95%; d. Boc$_2$O, Et$_3$N, CH$_2$Cl$_2$,85%; e. NaBH$_4$, LiCl, THF/EtOH,85%; f. SO$_3$.Pyr complex, DMSO, Et$_3$N, CH$_2$Cl$_2$; g. Na(AcO)$_3$BH, AcOH, CH$_2$Cl$_2$, 88%; h. HCl in dioxane, 90%; i. pyruvic acid BOP, NMM, CH$_2$Cl$_2$, 70%; j. LiOH.H$_2$O, THF/H$_2$O a. Li₂CO₃, BnBr, DMF, 85%; b. MeI, NaHMDS, CH₂Cl₂ 78%; c. TFA/CH₂Cl₂, 90%
d. Na(AcO)₃BH, AcOH, CH₂Cl₂, 88%; e. HCl in dioxane, 90%; f. pyruvic acid, BOP, NMM, CH₂Cl₂, 70%; g. H₂, Pd/C, 99%; h. didemnin macrocycle salt, DIEA, HATU, CH₂Cl₂, 72% a. EtOH, SOCl₂, 95%; b. Boc₂O, Et₃N, CH₂Cl₂, 75%; c. MsCl, pyr., CH₂Cl₂, 86%; d. Se₂Ph₂, NaBH₄, EtOH, 86%; e. Pyr., H₂O₂, CH₂Cl₂, 82%; f. LiOH.H₂O, THF/H₂O, 95%; g. N-Me-D-Leucine methyl ester, BOP, NMM, CH₂Cl₂, 75%; h. HCl.dioxane; i. DB macrocycle salt, DIEA, HATU, CH₂Cl₂, 72%; j. HCl gas; k. NaHCO₃, ethyl acetate

DEOXO-PROLINE-CONTAINING TAMANDARIN AND DIDEMNIN ANALOGS, DEHYDRO-PROLINE-CONTAINING TAMANDARIN AND DIDEMNIN ANALOGS, AND METHODS OF MAKING AND USING THEM

CROSS-REFERENCE TO RELATED APPLICATIONS

This application is a continuation of U.S. patent application Ser. No. 09/767,080, filed Jan. 22, 2001, now U.S. Pat. No. 7,064,105 B2, which is a continuation-in-part of U.S. patent application Ser. No. 09/545,848, filed Apr. 7, 2000, now U.S. Pat. No. 6,509,315 B1.

STATEMENT REGARDING FEDERALLY SUPPORTED RESEARCH OR DEVELOPMENT

This research was supported in part by U.S. Government funds (NIH grant number CA40081), and the U.S. Government may therefore have certain rights in the invention.

BACKGROUND OF THE INVENTION

Didemnin B is a macrocyclic depsipeptide isolated from a species of marine tunicate. Didemnin B exhibits potent antiviral, immunosuppressive, and anti-tumor activities in vitro and in vivo, and was the first marine natural product to enter clinical testing against human cancers (Li et al., 1992, Studies in Natural Products Chemistry, 10:241-302; Sakai et al., 1996, J. Med. Chem. 39:2819-2834; Wipf, 1995, Chem. Rev. 95:2115-2134). Didemnin B is a didemnin, a family of compounds which potently inhibit protein synthesis and cell cycle progression, and induce more rapid apoptosis than any other natural products that has been isolated to date (Grubb et al., 1995, Biochem. Biophys, Res. Commun. 215:1130-1136; Johnson et al., 1996, FEBS Lett. 383:1-5; Johnson et al., 1999, Immunol. Cell Biol. 77:242-248; Johnson et al., 1999, J. Cell. Biochem. 72:269-278). Other members of this family of compounds, including didemnin M and dehydrodidemnin B, exhibit cytotoxic and cytostatic effects as well.

Tamandarin A (also designated {(2S)Hiv$^2$}didemnin B) is a naturally occurring didemnin congener which has recently been isolated from a marine tunicate. Tamandarin A exhibits biological activity which is analogous to the activities exhibited didemnin B. For example, tamandarin A is a potent inhibitor of protein synthesis, cell growth, and tumorigenesis. Tamandarin A exhibits greater in vitro activity against pancreatic carcinoma than does didemnin B (Liang et al., 1999, Org. Lett. 1: 1319-1322). A significant limitation on use of tamandarin A, either for research or for practical applications, is the limited supply of tamandarin A that is available from natural sources and the difficulty and expense of isolating this product. A need exists for a method of synthesizing tamandarin A and other didemnin analogs (including dehydrodidemnin analogs).

Despite the potency of didemnin B in isolated studies, its clinical effectiveness is hampered by side effects associated with therapeutic doses of the compound. As with many antiproliferative agents, didemnin B exhibits a relatively narrow therapeutic window. Although didemnin M and dehydrodidemnin B exhibit improved therapeutic potential, relative to didemnin B, a need still exists for anti-proliferative agents which exhibit less toxicity at a therapeutic dose (i.e. didemnin analogs having a greater therapeutic index).

The present invention satisfies the needs set forth above.

BRIEF SUMMARY OF THE INVENTION

The invention relates to tamandarin and didemnin analogs that have a deoxo-proline residue or a dehydro-proline residue in their structure. In one embodiment, the invention relates to a composition comprising a tamandarin analog having the structure of formula I

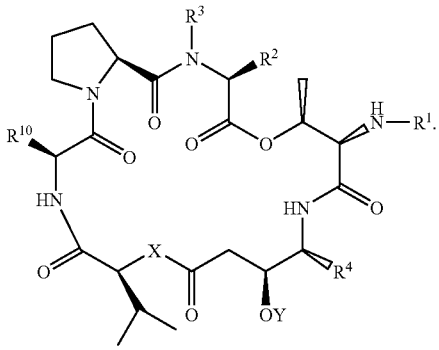

(I)

In formula I, R$^1$ is selected from the group consisting of
—(N-methyl)leucine-deoxo-proline,
—(N-methyl)leucine-deoxo-proline-lactate,
—(N-methyl)leucine-deoxo-proline-pyruvate,
—(N-methyl)leucine-deoxo-proline-lactate-(a first fluorophore),
—(N-methyl)leucine-deoxo-proline-lactate-glutamine-pyroglutamate,
—(N-methyl)leucine-deoxo-proline-lactate-glutamine-cyclopentanoate,
—(N-methyl)leucine-deoxo-proline-alanine-leucine-pyroglutamate, and
—(N-methyl)leucine-deoxo-proline-(N-methyl-alanine)-leucine-pyroglutamate,
—(N-methyl)leucine-dehydro-proline,
—(N-methyl)leucine-dehydro-proline-lactate,
—(N-methyl)leucine-dehydro-proline-pyruvate,
—(N-methyl)leucine-dehydro-proline-lactate-(a first fluorophore),
—(N-methyl)leucine-dehydro-proline-lactate-glutamine-pyroglutamate,
—(N-methyl)leucine-dehydro-proline-lactate-glutamine-cyclopentanoate,
—(N-methyl)leucine-dehydro-proline-alanine-leucine-pyroglutamate, and
—(N-methyl)leucine-dehydro-proline-(N-methyl-alanine)-leucine-pyroglutamate.

R$^2$ and R$^3$ in formula I, can be separate moieties or they can, together, be a single moiety. When R$^2$ and R$^3$ are separate moieties, R$^3$ is either a methyl group or a hydride radical and R$^2$ is selected from the group consisting of an isoleucine side chain, a valine side chain, an alanine side chain, a norleucine side chain, a norvaline side chain, leucine side chain, a histidine side chain, a tryptophan side chain, an arginine side chain, a lysine side chain, a second fluorophore, and a substituent having the structure of formula III

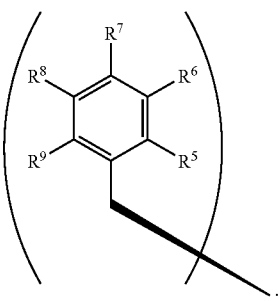
(III)

When R² and R³ are, together, a single substituent, this substituent has the structure of formula IV

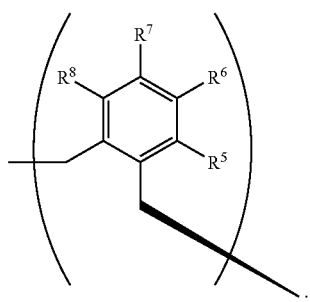
(IV)

In formulas III and IV, each of R⁵, R⁶, R⁷, R⁸, and R⁹ is independently selected from the group consisting of —H, —OH, —OCH₃, —CO(C₆H₅), —Br, —I, —F, —Cl, —CH₃, and —C₂H₅.

R⁴ in formula I is either an isoleucine side chain or a valine side chain. Also, in formula I, X is either —O— or —(NH)—, Y is either a hydride radical or a hydroxyl protecting group, and R¹⁰ is either a leucine side chain or a lysine side chain. The didemnin analog is an analog other than tamandarin A (i.e. {(2S)Hiv²}didemnin B). In one embodiment, every proline or lactate moiety that is present in R¹ exhibits (S) stereochemistry. In another, every moiety capable of exhibiting stereochemistry in R¹ is present in its naturally occurring form (i.e. the (S) form for amino acid residues and lactate. It is believed that cyclopentanoate occurs naturally in an (S) stereochemistry.

In another embodiment, the invention relates to a composition comprising a didemnin analog having the structure of formula XXI

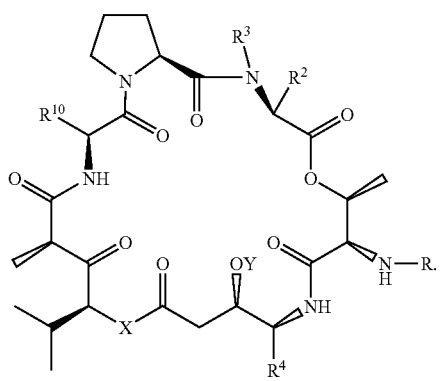
(XXI)

In formula XXI, each of R¹, R², R³, R⁴, R⁵, R⁶, R⁷, R⁸, R⁹, and R¹⁰ has the same meaning as in formula I.

In preferred classes of deoxo-proline tamandarin and didemnin analogs having the formula of I and XXI, respectively, R² has the structure of formula III, R³ is methyl, R⁴ is an isoleucine side chain, each of R⁵, R⁶, R⁸, and R⁹ is a hydride radical, R⁷ is methoxy, R¹⁰ is a leucine side chain, X is —O—, and Y is a hydride radical. Examples of tamandarin and didemnin analogs that are included in the invention are compounds 201, 202, 203, and 204, which are shown in FIGS. 1, 2, 7, and 8 respectively.

In one embodiment, the tamandarin or didemnin analog has a photoreactive substituent, such as an R² moiety having the structure

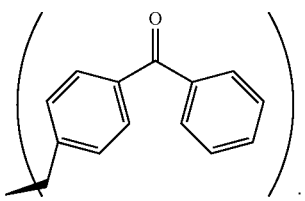

In another embodiment, the tamandarin or didemnin analog has a fluorophore attached, such as an analog in which a fluorophore is attached at the omega amino moiety of a lysine side chain at R² or at R¹⁰. Alternatively, the didemnin analog can be attached (e.g. covalently) with a support. In most embodiments, Y in formulas I and XXI is preferably a hydride radical.

The invention includes an embodiment of a tamandarin or didemnin analog which can be activated (or the activity of which can be enhanced) by enzymatic cleavage of a moiety bound with the analog. For example, the invention includes compositions which comprise a tamandarin analog having a structure selected from the group consisting of formulas (a)-(d), as follows.

(a)
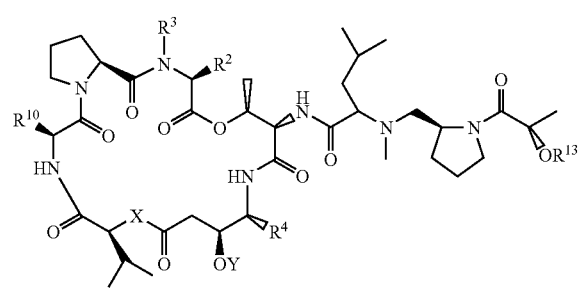

(b)
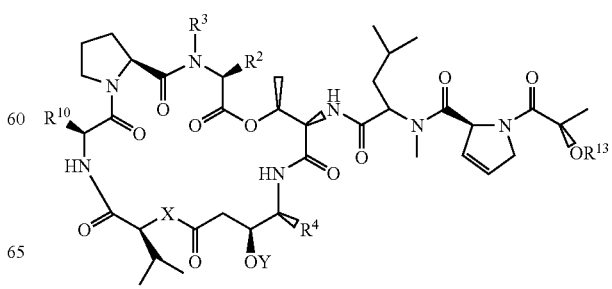

(c)

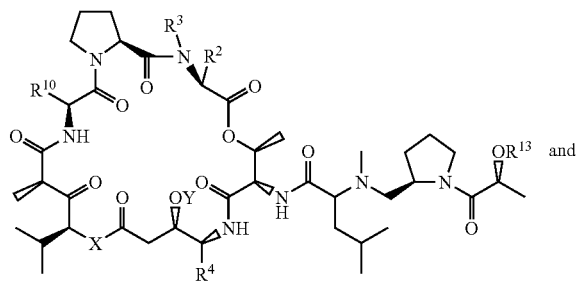

(d)

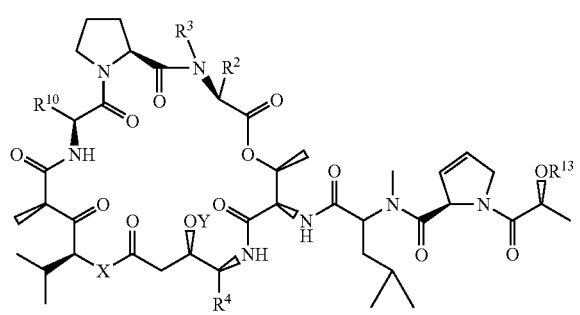

In formulas (a)-(d), $R^2$, $R^3$, $R^4$, $R^{10}$, X, and Y have the same identities described above for formula I. $R^{13}$ is an enzyme-cleavable moiety that is cleavable by an enzyme, such as one selected from the group consisting of a carboxypeptidase, a beta-lactamase, a beta-galactosidase, a penicillin V-amidase, a cytosine deaminase, a nitroreductase, a alkaline phosphatase, a beta-glucuronidase, and a catalytic antibody. By way of example, $R^{13}$ can have the structure of either of formulas V and VI (V)

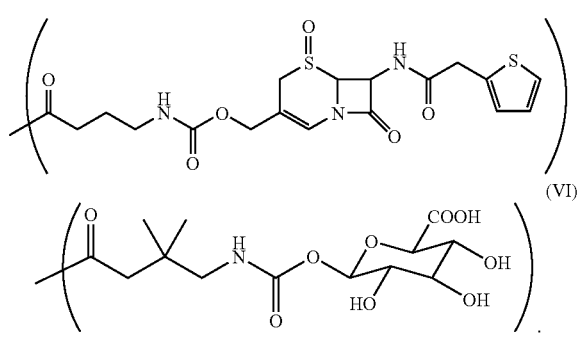

(VI)

The tamandarin and didemnin analogs described herein can be formulated, together with one or more pharmaceutically acceptable carriers, to make pharmaceutical preparations. These preparations can be administered to a mammalian (e.g. human) cell (i.e. either in vitro or in vivo) in order to inhibit protein synthesis, inhibit growth, inhibit proliferation, inhibit tumorigenesis, or enhance apoptosis in the cell or in one or more tissues of the mammal.

The invention further relates to a method of making deoxo-proline-containing tamandarin and didemnin analogs. These methods employ known methods for making tamandarin and didemnin analogs, and are modified to incorporate a deoxo-proline residue in place of a proline residue of the analog.

The invention still further relates to a method of making dehydro-proline-containing tamandarin and didemnin analogs. These methods employ known methods for making tamandarin and didemnin analogs, and are modified to incorporate a dehydro-proline residue in place of a proline residue of the analog.

BRIEF DESCRIPTION OF THE DRAWINGS

Each of FIG. 3, FIG. 4.

DETAILED DESCRIPTION OF THE INVENTION

Figure 1:
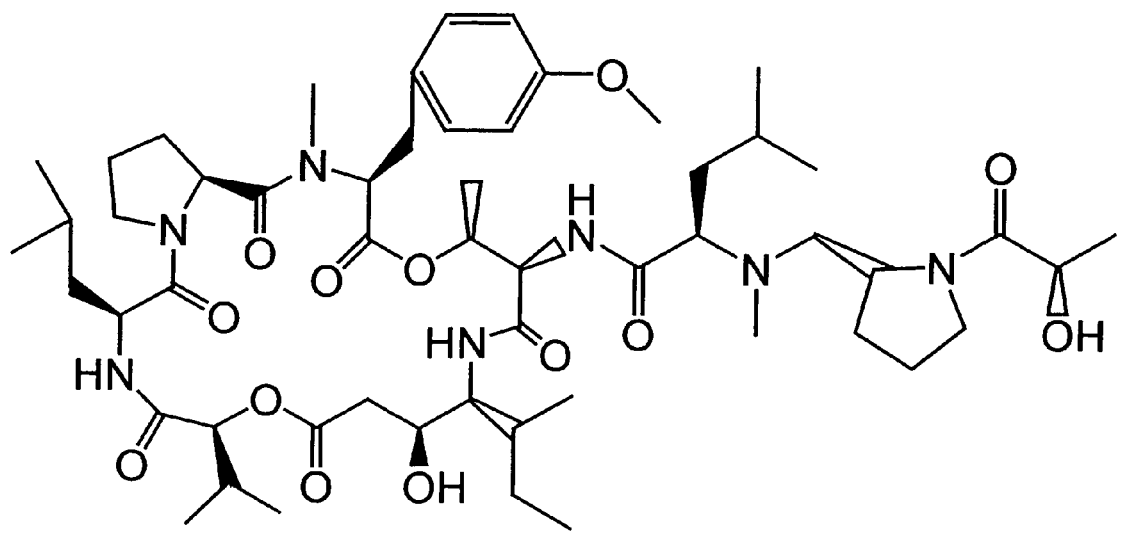
FIG. 1 is the structure of a preferred deoxo-proline tamandarin analog designated compound 201.
Figure 2:
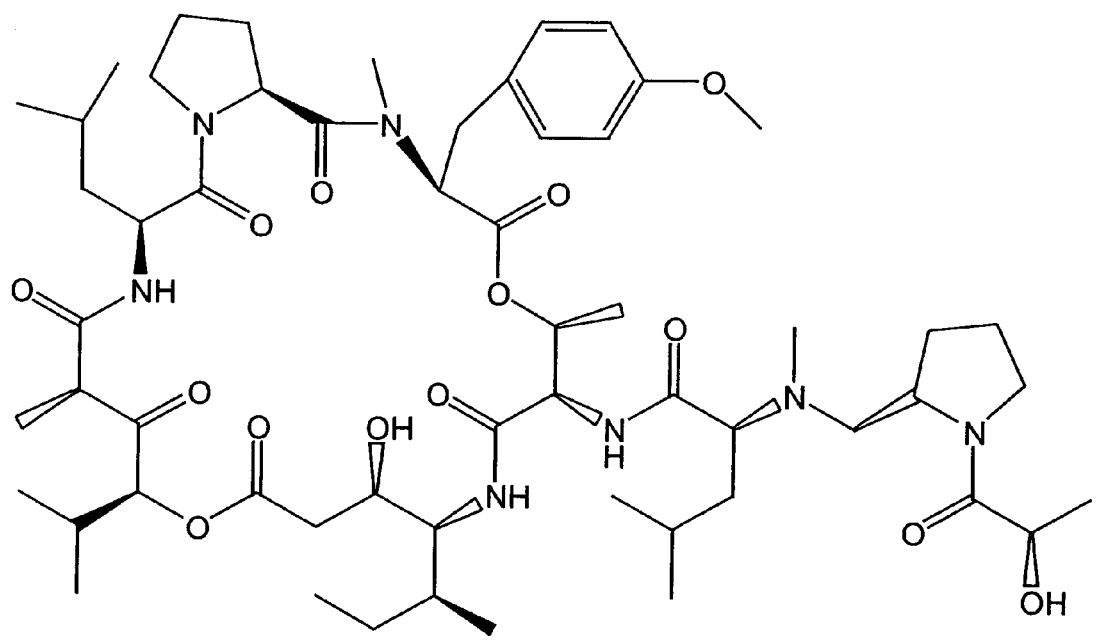
FIG. 2 is the structure of a preferred deoxo-proline didemnin analog designated compound 202.

The invention relates to tamandarin and didemnin analogs which have a deoxo-proline residue or a dehydro-proline residue in their structure. The invention includes compositions comprising these deoxo-proline or dehydro-proline tamandarin and didemnin analogs, and methods for making and using these analogs. These analogs are useful for, among other things, inhibiting protein synthesis, cell growth, cell proliferation, and tumorigenesis. The analogs of the invention can also exhibit anti-viral, anti-tumor, apoptosis-inducing, and immunosuppressive activities in animals, including in humans.

The invention includes compositions comprising a tamandarin analog having the structure

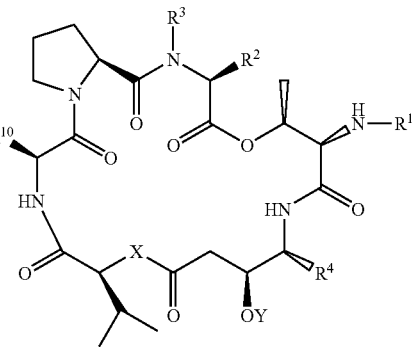

wherein $R^1$, $R^2$, $R^3$, $R^4$, $R^{10}$, X, and Y have the identities described herein.

The invention also includes compositions comprising a didemnin analog having the structure

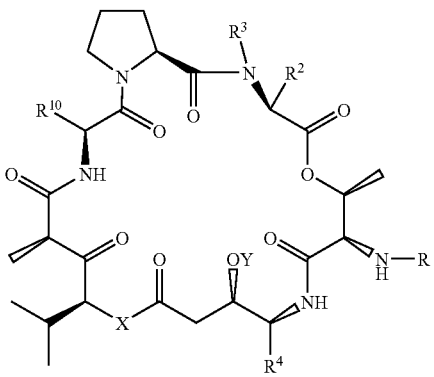

wherein $R^1$, $R^2$, $R^3$, $R^4$, $R^{10}$, X and Y have the identities described herein.

DEFINITIONS

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

As used herein, amino acid residues are represented by the full name thereof, by the three letter code corresponding thereto, or by the one-letter code corresponding thereto, as indicated by the following:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

As used herein, the term "amino acid side chain" refers to a moiety comprising all of the atoms of an amino acid excluding the alpha-carbon atom, a hydrogen atom bound with the alpha-carbon, the atoms of the alpha-carboxyl moiety and the alpha-amine moiety. By way of example, an "alanine side chain" refers to a methyl group, and a "valine side chain" refers to a 2-propyl group.

"Inhibition" of a process in a cell (e.g. inhibition of protein synthesis, inhibition of cell growth, inhibition of cell cycle progression, inhibition of cell proliferation, or inhibition of tumorigenesis) means reduction (e.g. by at least 10%, 25%, 50%, 75%, 90%, 95%, or even 100%) of the rate at which the process proceeds, reduction (e.g. by at least 10%, 25%, 50%, 75%, 90%, 95%, or even 100%) of the rate at which the process is initiated, or both.

"Enhancement" of a process in a cell (e.g. enhancement of apoptosis) means increasing (e.g. by at least 10%, 25%, 50%, 75%, 90%, 95%, or even 100%) the rate at which the process proceeds, increasing (e.g. by at least 10%, 25%, 50%, 75%, 90%, 95%, or even 100%) the rate at which the process is initiated, or both.

As used herein, the term "pharmaceutically acceptable carrier" means a chemical composition with which a didemnin analog or fragment, as described herein, can be combined and which, following the combination, can be administered to a subject (e.g. a human or other animal).

As used herein, the term "physiologically acceptable" ester or salt means an ester or salt form of a didemnin analog or fragment, as described herein, which is compatible with other ingredients of a pharmaceutical composition and which is not deleterious to a subject to which the composition is to be administered.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration can include, but is not limited to, subcutaneous, intraperitoneal, intramuscular, intrasternal injection, and kidney dialytic infusion techniques.

As used herein, the term "anti-viral activity" means preventing replication of a virus in the cell, preventing infection of the cell by a virus, or reversing a physiological effect of infection of the cell by a virus. An anti-viral agent a composition of matter which, when delivered to a cell, exhibits anti-viral activities. Anti-viral agents are well known and described in the literature. By way of example, AZT (zidovudine, RETROVIR® Glaxo Weilcome Inc., Research Triangle Park, N.C.) is an anti-viral agent which is thought to prevent replication of HIV in human cells.

As used herein, a "deoxo-proline" moiety or residue is a chemical moiety which has the following structure.

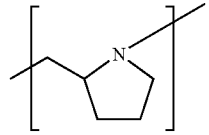

As used herein, a "dehydro-proline" moiety or residue is a chemical moiety which has the following structure.

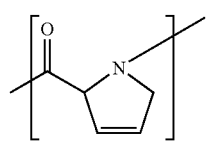

Description

The present invention relates to tamandarin and didemnin analogs having a deoxo-proline moiety or a dehydro-proline in their structure. These analogs exhibit potent pharmacological properties when administered to humans and other mammals. By way of example, these compounds can inhibit protein synthesis and cell growth and proliferation. These compounds can also enhance apoptosis in cells. These properties render the compounds useful for treating a variety of disorders which are characterized by one or more of aberrant protein synthesis, aberrant cell growth, aberrant proliferation of cells, and aberrant apoptosis. Examples of such disorders include tumorigenesis, tumor growth, tumor metastasis, infection of a cell by a virus, replication of a virus within a cell.

Among the compositions of the inventions are those which comprise a tamandarin analog having the structure of formula I or a didemnin analog having the structure of formula XXI.

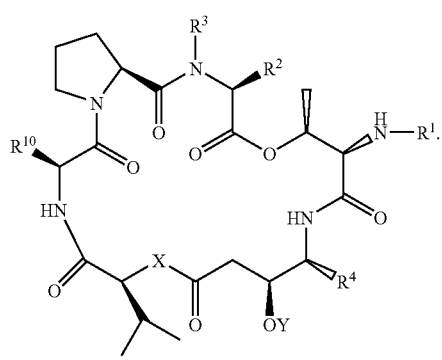

(I)

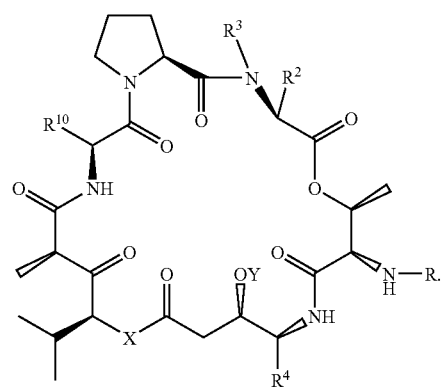

(XXI)

The $R^1$ substituent of formulas I and XXI has a deoxo-proline moiety in its structure, and can, for example, be a polypeptide comprising one or more amino acid residues in addition to the deoxo-proline residue. Examples of such polypeptides include —(N-methyl)leucine-deoxo-proline,
—(N-methyl)leucine-deoxo-proline-lactate,
—(N-methyl)leucine-deoxo-proline-pyruvate,
—(N-methyl)leucine-deoxo-proline-lactate-glutamine-pyroglutamate,
—(N-methyl)leucine-deoxo-proline-lactate-glutamine-cyclopentanoate,
—(N-methyl)leucine-deoxo-proline-lactate-leucine-pyroglutamate,
—(N-methyl)leucine-deoxo-proline-alanine-leucine-pyroglutamate, and
—(N-methyl)leucine-deoxo-proline-(N-methyl)alanine-leucine-pyroglutamate,
—(N-methyl)leucine-dehydro-proline,
—(N-methyl)leucine-dehydro-proline-lactate,
—(N-methyl)leucine-dehydro-proline-pyruvate,
—(N-methyl)leucine-dehydro-proline-lactate-(a first fluorophore),
—(N-methyl)leucine-dehydro-proline-lactate-glutamine-pyroglutamate,
—(N-methyl)leucine-dehydro-proline-lactate-glutamine-cyclopentanoate,
—(N-methyl)leucine-dehydro-proline-alanine-leucine-pyroglutamate, and
—(N-methyl)leucine-dehydro-proline-(N-methyl-alanine)-leucine-pyroglutamate.

Additional examples of alternative $R^1$ substituents include deoxo-proline-containing peptides which comprise a fluorophore (e.g., rhodamine or coumarin), an enzymatically-cleavable group, or another chemical moiety bound (e.g. covalently attached) with a support (e.g. a glass or silica plate, an agarose or other polymeric bead, etc.). When $R^1$ comprises an N-methyl-leucine residue, the alpha-carbon atom of that residue can have either (R) or (S) stereochemistry. Other amino acid residues within $R^1$ can have either (R) or (S) stereochemistry, but they preferably have (S) stereochemistry at their alpha-carbon atom. When $R^1$ comprises a lactate residue, the lactate residue is preferably an (S)lactate residue. In a preferable embodiment, every amino acid residue within $R^1$ other than the leucine (or N-methyl-leucine) residue (if present) attached directly to the nitrogen atom of the ring of formula I or XXI has (S) stereochemistry.

$R^3$ can be either of —$CH_3$ and —H. Alternatively, $R^3$ can, together with $R^2$, be a single substituent.

The $R^2$ substituent can be an amino acid side chain such as an isoleucine side chain (i.e. a 2-butyl moiety, preferably having (R) stereochemistry), a valine side chain (i.e. a 2-propyl moiety), an alanine side chain (i.e. a methyl moiety), a norleucine side chain (i.e. a 1-butyl moiety), a norvaline side chain (i.e. a 1-propyl moiety), a leucine side chain (i.e. an isobutyl moiety, preferably having (S) stereochemistry), a phenylalanine side chain (i.e. a phenylmethyl moiety), a histidine side chain (i.e. a 4-methyl-imidazole moiety), a tryptophan side chain (i.e. a 3-methyl-indole moiety), a tyrosine side chain (i.e. a 4-hydroxy-phenylmethyl moiety), an arginine side chain (i.e. a 4-guanidinyl-butyl moiety), and a lysine side chain (i.e. a 4-aminobutyl moiety).

An $R^2$ substituent can comprise a fluorophore (e.g. a fluorophore linked with one of the amino acid side chains described above). In addition, $R^2$ substituent can have the structure of formula III

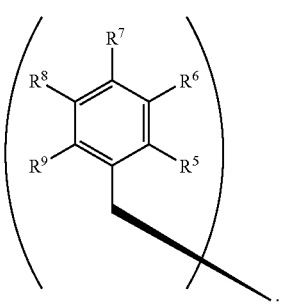

(III)

In an alternative embodiment, $R^2$ and $R^3$ together are a substituent having the structure of formula IV

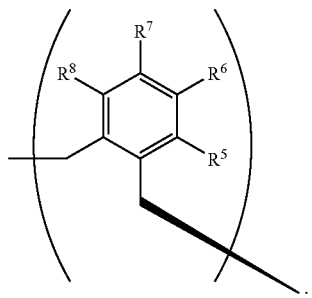

(IV)

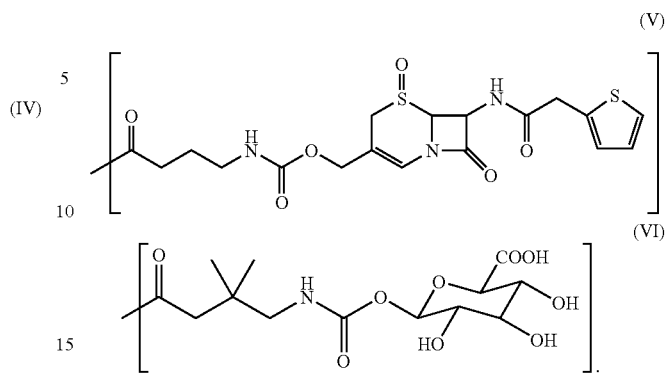

(V)

(VI)

In formulas III and IV, each of $R^5$, $R^6$, $R^7$, $R^8$, and $R^9$, independently, can be a substituent selected from the group consisting of —H, —OH, —OCH$_3$, —CO(C$_6$H$_5$), —Br, —I, —F, —Cl, —CH$_3$, and —CH$_2$CH$_3$.

$R^4$ can be an isoleucine side chain or a valine side chain.

X can be —O— or —(NH)—.

Y can be —H or a hydroxyl protecting group. Examples of hydroxyl protecting groups which can be present at Y include an alkyl-substituted silyl moiety, an aryl-substituted silyl moiety, or a silane substituted with both alkyl- and aryl-moieties. An example of a useful hydroxyl protecting group is a triisopropylsilyl moiety. Other hydroxyl protecting groups which can be used at Y in formula I are described in references such as Green and Wutz (1999, *Protecting Groups in Organic Synthesis*, Wiley, New York).

$R^{10}$ can be an amino acid side chain such as a leucine side chain or a lysine side chain. Alternatively, $R^{10}$ can be an amino acid or other chemical moiety which is bound with (e.g. covalently attached to) a support (e.g. a solid support).

Another group of compositions included within the invention are those which comprise a deoxo-proline tamandarin analog having a structure selected from the group consisting of formulas (a)-(d), set forth above.

Each of $R^2$, $R^3$, $R^4$, $R^{10}$, X, and Y has the same meaning in formulas (a)-(d) that it has in formulas I and XXI.

In formulas (a)-(d), $R^{13}$ can be hydrogen or a chemical moiety which can be enzymatically cleavable (i.e. an enzyme-cleavable moiety). As used herein, an enzyme-cleavable moiety can include any chemical moiety which can be cleaved (i.e. chemically detached from) in the presence of a specific enzyme. Examples of enzymes capable of chemically detaching an enzyme-cleavable moiety include carboxypeptidases, beta-lactamase, beta-galactosidase, penicillin V-amidase, cytosine deaminase, nitroreductase, alkaline phosphatase, beta-glucuronidase, and catalytic antibodies. Examples of enzyme-cleavable moieties which can be incorporated in a compound described herein include cephalosporins, beta-glucosides, phosphate, pyrophosphate, beta-D-galactosides, nitrobenzamidine, cytosine, carbamates, peptides, and amino acids. Alternatively, $R^{13}$ can be an enzyme-cleavable moiety such as a di-peptide linked with glutamine-pyro-glutamate, or a moiety having the structure of formula V or formula VI After cleavage of an enzyme-cleavable moiety by an enzyme, the resulting didemnin analog can exhibit one or more of the physiological activities described herein. A tamandarin or didemnin analog having the structure of one of formulas (a)-(d), wherein $R^{13}$ is an enzyme-cleavable moiety, can, optionally, exhibit these activities before the cleavage of the enzyme-cleavable moiety. However, in a preferred embodiment, the analog exhibits therapeutic activity only following cleavage of the enzyme-cleavable moiety therefrom.

As described above, a tamandarin or didemnin analog having the structure of one of formulas I, XXI, and (a)-(d) can be bound with a support. The identity of the support is not critical. The support can be substantially any material with which such an analog can be bound (e.g. by covalent attachment through one of the $R^{10}$ or $R^1$ moieties). Examples of support materials include bonded silicates, cross-linked agarose, polyacrylamide, dextran, and allyl dextran. Such support materials can be chemically modified using reactive chemical moieties in order to facilitate covalent attachment of the analog with the support. Chemical modifications of this type are known in the art, and can, for example, include modification of a support with cyanogen bromide groups, epoxide groups, mesyl groups, and carboxyhexyl groups. Protocols for preparation of a support and subsequent attachment of a compound to the support are available in the art, and can be modified by one skilled in the art for use with a didemnin analog described herein.

Preferred tamandarin analogs are based on the structure of tamandarin A. In these analogs, $R^2$ is an O-methyl-tyrosine side chain (i.e. $R^5$, $R^6$, $R^8$, and $R^9$ are each —H, and $R^7$ is —OCH$_3$), $R^3$ is —CH$_3$, $R^4$ is an isoleucine side chain, $R^{10}$ is a leucine side chain, X is —O—, and Y is —H.

Preferred didemnin analogs are based on the structure of didemnin B. In these analogs, $R^2$ is an O-methyl-tyrosine side chain (i.e. $R^5$, $R^6$, $R^8$, and $R^9$ are each —H, and $R^7$ is —OCH$_3$), $R^3$ is —CH$_3$, $R^4$ is an isoleucine side chain, $R^{10}$ is a leucine side chain, X is —O—, and Y is —H.

Methods of Using Compounds Described Herein

Deoxo-proline-containing tamandarin and didemnin analogs and dehydro-proline-containing tamandarin and didemnin analogs, as each are disclosed herein, can be used to affect a variety of physiological processes. Each of these types of compounds can be used to inhibit protein synthesis. Furthermore, the compounds can be used to inhibit progression of a cell through the cell cycle. While not being bound by any particular theory of operation, it is believed that the cell cycle-inhibiting activity of the compounds can be attributed to inhibition of protein synthesis and possibly also to inhibition of other cellular activities associated with DNA replication or cell division. These tamandarin and didemnin analogs also induce apoptosis in cells. The physiological activities attributable to these tamandarin and didemnin analogs make these compounds useful for alleviating a variety of disorders in which one or more of cell growth, proliferation, and survival are aberrant. Examples of such disorders include cancers at various stages (e.g. tumorigenesis, tumor growth, and metastasis) and viral infections at various stages (e.g. infection of cells with virus particles, production of virus particles within a cell, and survival of virus-infected cells).

While still not being bound by any particular theory of operation, it is believed that the physiological activities attributable to the tamandarin and didemnin analogs described herein result from one or more interactions between such analogs and at least one cellular component. This interaction(s) leads, directly or indirectly, to the observed cellular response. Accordingly, the invention encompasses use of these compounds to identify one or more cellular components which contributes to a disorder phenotype in an individual. Identification of such a cellular component can indicate an effective course of treatment for alleviating the disorder. Examples of compounds useful for this purpose include analogs which comprise a fluorescent substituent (e.g., at $R^1$ or $R^2$), a photoreactive chemical moiety, such as a moiety having the structure

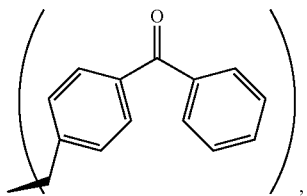

or a moiety bound with a support.

Fluorescent and other detectably labeled deoxo-proline tamandarin and didemnin analogs described herein (as well as their physiologically active fragments) can be used to identify cells in which those analogs and fragments can exert their physiological effects. For example, cells which absorb or bind with a fluorescent analog can be identified or isolated. Identification or isolation of such cells can be used to diagnose a disorder associated with the presence of such cells. Identification or isolation of these cells can also indicate which of the tamandarin or didemnin analogs are efficacious for treating a disorder involving the cells.

The tamandarin and didemnin analogs described herein can be used for anti-proliferative, anti-tumor, anti-viral, and immunosuppressive purposes. For example, these compounds can be used in a pharmaceutical preparation or medicament to be administered to a patient afflicted with a disorder in which one or more of protein synthesis, cell growth, proliferation, and survival are aberrant. Such medicaments can be used to treat disorders such as cancers (e.g. breast cancer), viral, fungal, parasitic, and bacterial infections, auto-immune disorders, allergies, other hyper-immune disorders, and atherosclerosis.

Examples of anti-tumor activities that can be exhibited by the compounds described herein include inhibition of tumorigenesis, inhibition of metastasis, inhibition of tumor cell growth, inhibition of tumor cell proliferation, and enhancement of tumor cell apoptosis. Dehydrodidemnin exhibits activity against cell lines derived from several human solid tumor types, including non-small cell lung cancer and colon tumor cell lines, and exhibits selective anti-tumor activity against non-small cell lung cancer, melanomas, ovarian cancer, and colorectal cancer (Depenbrock et al., 1998, Brit. J. of Cancer 78(6): 739-744). The tamandarin and didemnin analogs described herein exhibit anti-tumor activities in cells of one or more of these lines, as well as in cells of the corresponding tumor type in vivo. Determination of the effectiveness of any particular analog against any particular tumor type can be made using standard methods involving, for example, one or more of the 60 standard tumor cell lines maintained in the U.S. National Cancer Institute drug screening program.

Examples of anti-viral activities that can be exhibited by the tamandarin and didemnin analogs described herein include inhibition of binding of a virus with a cellular target, inhibition of infection of a cell by a virus, inhibition of cellular synthesis of virus components, inhibition of intracellular assembly of virus particles, inhibition of release of virus particles from an infected cell, inhibition of growth of a cell infected by a virus, inhibition of proliferation of a cell infected by a virus, and induction of death (i.e. apoptosis) of a cell infected by a virus. The anti-viral activity of the compounds described herein can, for example, be used to treat or prevent viral infections of mammals and associated symptoms. By way of illustration, a deoxo-proline-containing tamandarin or didemnin analog, or a dehydro-proline-containing tamandarin or didemnin analog, can be used to treat or prevent infections by viruses such as Rift Valley Fever virus, Dengue virus, or any of the equine encephalitis viruses.

Examples of immunosuppressive activities that can be exhibited by the tamandarin and didemnin analogs described herein include inhibition of a cellular immune response to an immunogen (e.g. an infectious agent, or a transplanted cell or tissue) and inhibition of a humoral immune response to an immunogen. Examples of disorders in which immunosupression can be desirable include autoimmune disorders, transplant rejection disorders (e.g. rejection of a solid tissue or bone marrow transplant), development of an immune response to an implanted device (e.g. a stent or a heart valve), immune hypersensitivity, and anaphylaxis.

The tamandarin and didemnin analogs described herein can be administered in vitro to a cell or tissue (e.g. a cultured cell or tissue, or a cell or tissue harvested from one animal prior to introduction into the same or a different animal). Alternatively, the analogs can be administered to the cell or tissue in vivo by administering the analog or a pharmaceutical composition comprising the analog to an animal (e.g. a mammal such as a human) that comprises the cell or tissue.

In one embodiment of the treatment methods described herein, a tamandarin or didemnin analog described herein and having an enzyme-cleavable group attached thereto (e.g. a compound having the structure of formula II) is administered to an animal. Upon cleavage of the enzyme-cleavable group, the compound is transformed from an inactive (or less active) form to an active (or more active) form. Thus, the deoxo-proline tamandarin or didemnin analog can be selectively activated at a body location at which the enzyme activity occurs.

The enzyme which is used to cleave a tamandarin or didemnin analog having an enzyme-cleavable moiety attached can be an enzyme which naturally occurs at a body location in an animal. Alternatively, the enzyme can be provided to the animal, for example as a composition comprising the enzyme or a nucleic acid which encodes the enzyme. As another example, the enzyme can be coupled (e.g. covalently, using a cross-linking agent or by expression as an enzyme-antibody fusion protein) with an antibody that specifically binds with a tissue (e.g. cancerous cells such as leukemic cells or cells of a solid tumor) at a body location in the animal, and the antibody-enzyme complex can be administered to an animal. Administration of a deoxo-proline tamandarin or didemnin analog having an attached enzyme-cleavable group to the same animal results in preferential activation of the compound at the tissue or body location. The physiological effect of the compound can thereby be localized at the tissue or body location, and any side effect attributable to the activated compound can thereby be reduced or minimized.

A support-bound tamandarin or didemnin analog can be used to identify cells which comprise, on their surfaces or elsewhere, receptor proteins, glycoproteins, and the like, which are capable of interacting or binding with the analog. As an example, a deoxo-proline tamandarin or didemnin analog having the structure of formula I or XXI and attached to a support can, by virtue of its interaction with a particular cellular receptor, be used to identify or physically isolate cells of a particular type (e.g. tumor cells) which are characterized by the presence of the particular receptor.

Methods of Making Compounds Described Herein

Methods of making tamandarin and didemnin analogs have been described (e.g., Harris et al., 1987, Tetrahedron Lett. 28:2837-2840; Harris et al., 1988, Tetrahedron 44:3489-3500; Ewing et al., 1986, Tetrahedron 42:5863-5868; Ewing, W. R., 1988, Ph.D. Dissertation, University of Pennsylvania, Philadelphia Pa.; Ewing et al., 1989, Tetrahedron Lett. 30:3757-3760; Li et al., 1990, J. Am. Chem. Soc. 112:7659-7672; Mayer et al., 1994, J. Org. Chem. 59:5192-5205; Mayer et al., 1994, Tetrahedron: Asymmetry 5:519-522; Xiao et al., 1997, Tetrahedron: Asymmetry 9:47-53; Pfizenmayer et al., 1998, 8:3653-3656; U.S. patent application Ser. No. 09/545, 848, filed Apr. 7, 2000). The contents of each of these references and patent application are incorporated herein by reference. The precise method used to make a tamandarin or didemnin macrocycle or analog is not critical.

What represents novel subject matter in this disclosure is incorporation of a deoxo-proline residue or a dehydro-proline residue in the side chain of a tamandarin or didemnin analog. The deoxo-proline residue or dehydro-proline residue can be used in place of a proline residue in any known tamandarin or didemnin analog. Particularly contemplated tamandarin and didemnin analogs are those in which the deoxo-proline residue or dehydro-proline residue is linked to the macrocycle by way of a leucine residue having a methylated amine moiety (i.e., an —(N-methyl)leucine-(deoxo or dehydro)-proline-containing tamandarin or didemnin analog). Of course, the (deoxo or dehydro)-proline residue can be further substituted, for example by lactate, by pyruvate, by lactate-fluorophore, by lactate-glutamine-pyroglutamate, by lactate-glutamine-cyclopentanoate, by -alanine-leucine-pyroglutamate, or by —(N-methyl-alanine)-leucine-pyroglutamate. One or more of the (deoxo or dehydro)-proline, lactate, glutamine, pyroglutamate, cyclopentanoate, and alanine residues is preferably the (S) enantiomer.

Incorporation of a deoxo-proline residue can be achieved by any method known in the art. Examples of methods of incorporating a deoxo-proline residue are included in this disclosure in Example 1 and in FIGS. 3-5.

In one embodiment, the method of incorporating a deoxo-proline residue comprises protecting the hydroxyl and amine moieties of leucine, methylating the leucine amine moiety, and de-protecting the leucine amine moiety. The amine group of proline is protected, and the ester function of the proline is reduced to an aldehyde (e.g., using a strong base such as LiBH$_4$ coupled with oxidation with an oxidizing agent such as pyridine-SO$_3$). Reductive amination (e.g., in the presence of a non-aqueous solvent, a strong base, and a carboxylic acid catalyst; e.g., in the presence of Na(AcO)$_3$BH, AcOH, and CH$_2$Cl$_2$) can be used to couple the hydroxyl-protected leucine with the amine protected proline (e.g., to form compound 43 in FIG. 5, in one embodiment). The reductive amination can, for example, be performed as described by Abdel-Magid and co-workers (e.g., Abdel-Magid et al., 1990, Tetrahedron Lett. 31:5595-5598; Abdel-Magid et al., 1990, Synlett. 537-539).

The resulting leucine-deoxo-proline dipeptide can be further substituted with other moieties (e.g., with -lactate, -pyruvate, -lactate-fluorophore, -lactate-glutamine-pyroglutamate, -lactate-glutamine-cyclopentanoate, -alanine-leucine-pyroglutamate, or —(N-methyl-alanine)-leucine-pyroglutamate), with (preferably) or without first removing the protecting groups. The leucine-deoxo-proline dipeptide (optionally further substituted) can be attached to a tamandarin or didemnin macrocycle in the position identified as R$^1$ in formulas I and XXI.

Figure 6:
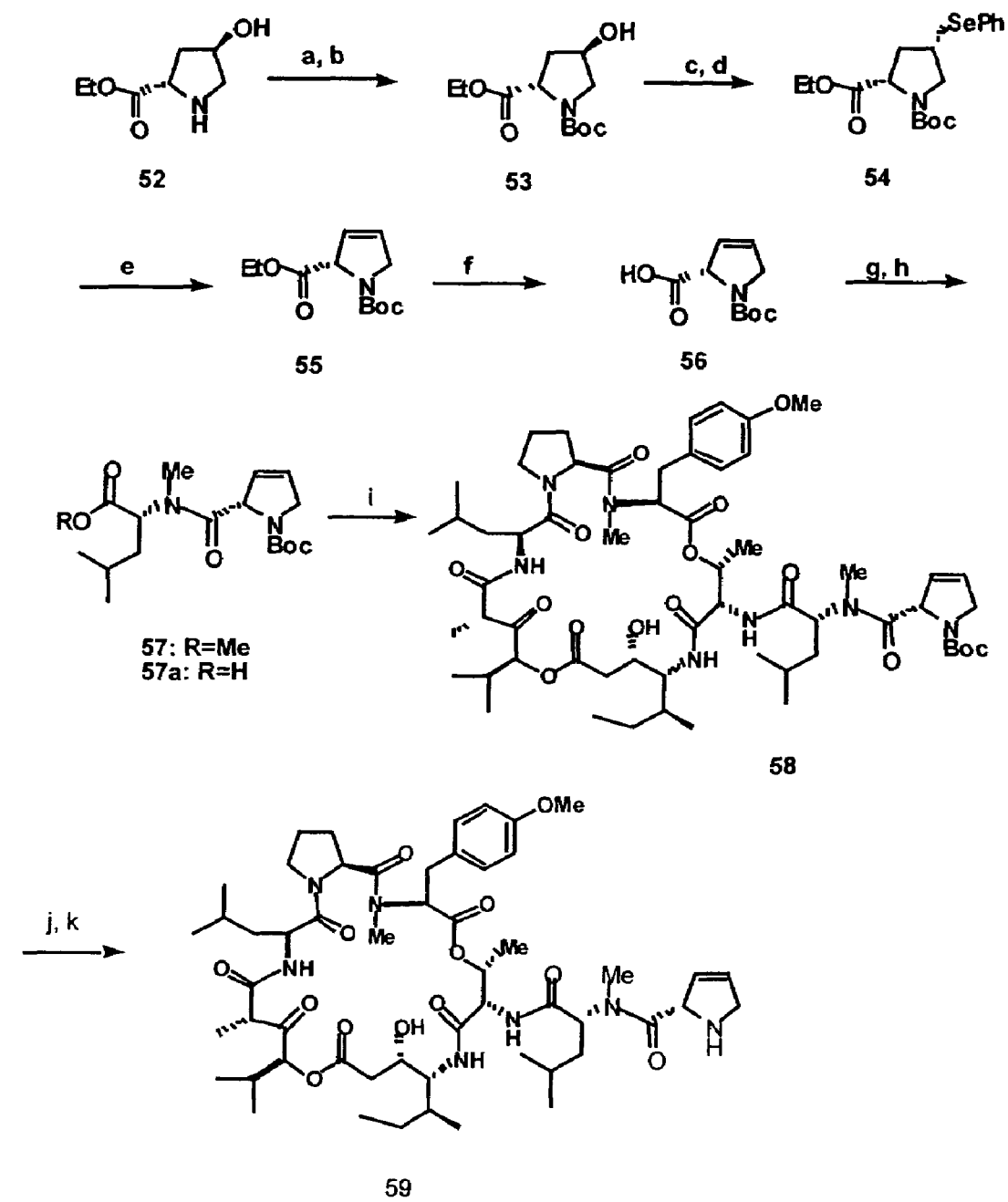
FIG. 6 depicts a method of making dehydro-proline-containing side chain moieties for tamandarin or didemnin analogs.
Figure 7:
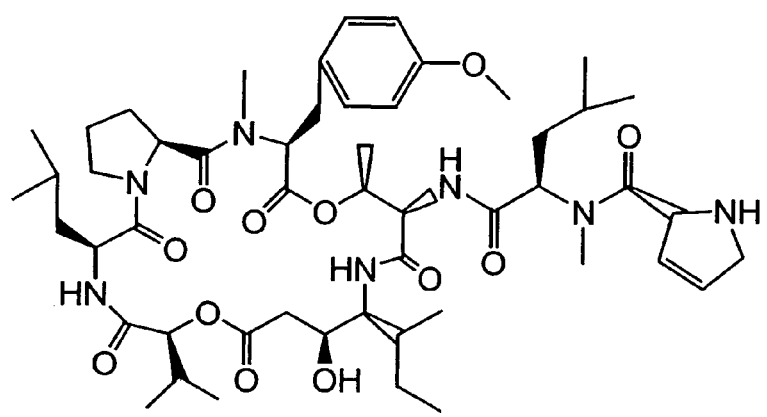
FIG. 7 is the structure of a preferred dehydro-proline tamandarin analog designated compound 203.
Figure 8:
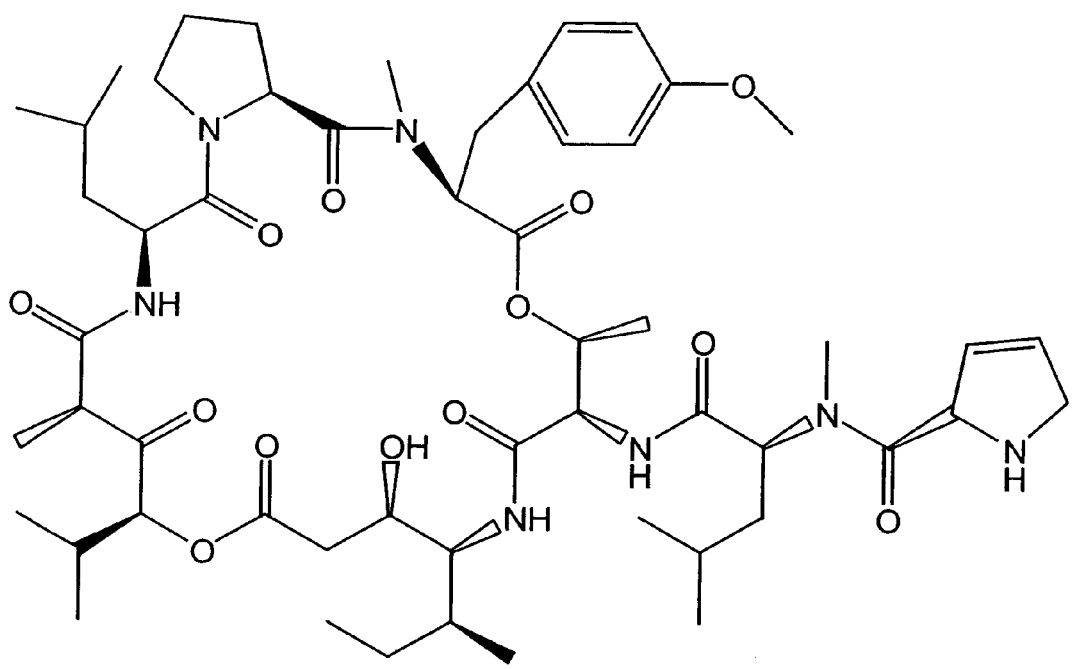
FIG. 8 is the structure of a preferred dehydro-proline didemnin analog designated compound 204.

Incorporation of a dehydro-proline residue can be achieved by any method known in the art. Examples of methods of incorporating a dehydro-proline residue are included in this disclosure in Example 2 and in FIG. 6.

In one embodiment, the method of incorporating a dehydro-proline residue comprises protecting the carboxyl and amino groups of 4-hydroxyprolinate, mesylating the 4-hydroxyl moiety, displacing the mesylate moiety with an aryl-selenyl moiety, oxidatively eliminating the aryl-selenyl moiety, and de-protecting the carboxyl moiety. The resulting dehydro-proline moiety can be coupled with one or more additional amino acid residues or organic acids (e.g., those identified herein, removing the amino-protecting group if necessary or desired) and coupled with a tamandarin or didemnin macrocycle made or obtained by conventional means.

Pharmaceutical Compositions

The invention encompasses pharmaceutical compositions comprising at least one of the deoxo-proline-containing tamandarin and didemnin analogs and dehydro-proline-containing tamandarin and didemnin analogs described herein. Such compositions can comprise the analog and a pharmaceutically acceptable carrier. By way of example, a pharmaceutical composition can comprise a pharmaceutically acceptable carrier and a tamandarin or didemnin analog having the structure of any of formulas I, II, and (a)-(d) as an active agent. As a further example, a pharmaceutical composition can comprise a pharmaceutically-acceptable carrier and one or more of the compounds depicted in the figures in this disclosure.

Such pharmaceutical compositions can be used, for example, in the methods described herein for and for inhibiting one or more of protein synthesis, cell cycle progression, tumorigenesis, growth, and proliferation in a cell. In addition, such compositions can be used in the methods described herein for enhancing apoptosis in a cell.

Pharmaceutical compositions that are useful in the methods of the invention can be administered systemically in oral solid formulations, ophthalmic, suppository, aerosol, topical or other similar formulations. In addition to the active agent, such pharmaceutical compositions can contain pharmaceutically-acceptable carriers and other ingredients known to enhance and facilitate drug administration. Other possible formulations, such as nanoparticles, liposomes, resealed erythrocytes, and immunologically based systems can also be used to administer the active agent according to the methods of the invention.

The invention encompasses pharmaceutical compositions which consist of the active agent, in a form suitable for administration to a subject, or the pharmaceutical composition can comprise the active agent and one or more pharmaceutically acceptable carriers, one or more additional ingredients, or some combination of these. The active agent can be present in the pharmaceutical composition in the form of a physiologically acceptable ester or salt, such as in combination with a physiologically acceptable cation or anion, as is well known in the art.

The formulations of the pharmaceutical compositions described herein can be prepared by any method known or hereafter developed in the art of pharmacology. In general, such preparatory methods include the step of bringing the active agent into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, and mammals including commercially relevant mammals such as cattle, pigs, horses, sheep, cats, and dogs.

Pharmaceutical compositions that are useful in the methods of the invention can be prepared, packaged, or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active agent, and immunologically-based formulations.

A pharmaceutical composition of the invention can be prepared, packaged, or sold in bulk, as a single unit dose, or as a plurality of single unit doses. As used herein, a "unit dose" is discrete amount of the pharmaceutical composition comprising a predetermined amount of the active agent. The amount of the active agent is generally equal to the dosage of the active agent which would be administered to a subject or a convenient fraction of such a dosage such as, for example, one-half or one-third of such a dosage.

In addition to the active agent, a pharmaceutical composition of the invention can further comprise one or more additional pharmaceutically active agents such as, other tumor therapy agents, other anti-infective agents, and the like.

Controlled- or sustained-release formulations of a pharmaceutical composition of the invention can be made using conventional technology.

A formulation of a pharmaceutical composition of the invention suitable for oral administration can be prepared, packaged, or sold in the form of a discrete solid dose unit including, but not limited to, a tablet, a hard or soft capsule, a cachet, a troche, or a lozenge, each containing a predetermined amount of the active agent. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active agent may, for example, be made by compressing or molding the active agent, optionally with one or more additional ingredients. Compressed tablets can be prepared by compressing, in a suitable device, the active agent in a free-flowing form such as a powder or granular preparation, optionally mixed with one or more of a binder, a lubricant, an excipient, a surface active agent, and a dispersing agent. Molded tablets can be made by molding, in a suitable device, a mixture of the active agent, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulfate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginate. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearate, silica, and talc.

Tablets can be non-coated or they can be coated using known methods to achieve delayed disintegration in the gastrointestinal tract of a subject, thereby providing sustained release and absorption of the active agent. By way of example, a material such as glyceryl monostearate or glyceryl distearate can be used to coat tablets. Further by way of example, tablets can be coated using methods described in U.S. Pat. Nos. 4,256,108; 4,160,452; and 4,265,874 to form osmotically-controlled release tablets. Tablets can further comprise a sweetening agent, a flavoring agent, a coloring agent, a preservative, or some combination of these in order to provide pharmaceutically elegant and palatable preparation.

Hard capsules comprising the active agent can be made using a physiologically degradable composition, such as gelatin. Such hard capsules comprise the active agent, and can further comprise additional ingredients including, for example, an inert solid diluent such as calcium carbonate, calcium phosphate, or kaolin.

Soft gelatin capsules comprising the active agent can be made using a physiologically degradable composition, such as gelatin. Such soft capsules comprise the active agent, which can be mixed with water or an oil medium such as peanut oil, liquid paraffin, or olive oil.

Liquid formulations of a pharmaceutical composition of the invention which are suitable for oral administration can be prepared, packaged, and sold either in liquid form or in the form of a dry product intended for reconstitution with water or another suitable vehicle prior to use.

Liquid suspensions can be prepared using conventional methods to achieve suspension of the active agent in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions can further comprise one or more additional ingredients including, but not limited to, suspending agents, dispersing or wetting agents, emulsifying agents, demulcents, preservatives, buffers, salts, flavorings, coloring agents, and sweetening agents. Oily suspensions can further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbate, and sorbate. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active agent in aqueous or oily solvents can be prepared in substantially the same manner as liquid suspensions, the primary difference being that the active agent is dissolved, rather than suspended in the solvent. Liquid solutions of the pharmaceutical composition of the invention can comprise each of the components described with regard to liquid suspensions, it being understood that suspending agents will not necessarily aid dissolution of the active agent in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention can be prepared using known methods. Such formulations can be administered directly to a subject, used, for example, to form tablets, to fill capsules, or to prepare an aqueous or oily suspension or solution by addition of an aqueous or oily vehicle thereto. Each of these formulations can further comprise one or more of dispersing or wetting agent, a suspending agent, and a preservative. Additional excipients, such as fillers and sweetening, flavoring, or coloring agents, can also be included in these formulations.

A pharmaceutical composition of the invention can also be prepared, packaged, or sold in the form of oil-in-water emulsion or a water-in-oil emulsion. The oily phase can be a vegetable oil such as olive or arachis oil, a mineral oil such as liquid paraffin, or a combination of these. Such compositions can further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions can also contain additional ingredients including, for example, sweetening or flavoring agents.

A pharmaceutical composition of the invention can be prepared, packaged, or sold in a formulation suitable for rectal administration. Such a composition can be in the form of, for example, a suppository, a retention enema preparation, and a solution for rectal or colonic irrigation.

Suppository formulations can be made by combining the active agent with a non-irritating pharmaceutically acceptable excipient which is solid at ordinary room temperature (i.e. about 20° C.) and which is liquid at the rectal temperature of the subject (i.e. about 37° C. in a healthy human). Suitable pharmaceutically acceptable excipients include, but are not limited to, cocoa butter, polyethylene glycols, and various glycerides. Suppository formulations can further comprise various additional ingredients including, but not limited to, antioxidants and preservatives.

Retention enema preparations or solutions for rectal or colonic irrigation can be made by combining the active agent with a pharmaceutically acceptable liquid carrier. As is well known in the art, enema preparations can be administered using, and can be packaged within, a delivery device adapted to the rectal anatomy of the subject. Enema preparations can further comprise various additional ingredients including, but not limited to, antioxidants and preservatives.

A pharmaceutical composition of the invention can be prepared, packaged, or sold in a formulation suitable for vaginal administration. Such a composition can be in the form of, for example, a suppository, an impregnated or coated vaginally-insertable material such as a tampon, a douche preparation, or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation can be made by combining the active agent with a pharmaceutically acceptable liquid carrier. As is well known in the art, douche preparations can be administered using, and can be packaged within, a delivery device adapted to the vaginal anatomy of the subject. Douche preparations can further comprise various additional ingredients including, but not limited to, antioxidants, antibiotics, anti-fungal agents, and preservatives.

Formulations of a pharmaceutical composition suitable for parenteral administration can comprise the active agent combined with a pharmaceutically acceptable carrier, such as sterile water or sterile isotonic saline. Such formulations can be prepared, packaged, or sold in a form suitable for bolus administration or for continuous administration. Injectable formulations can be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations can further comprise one or more additional ingredients including, but not limited to, suspending, stabilizing, or dispersing agents. In one embodiment of a formulation for parenteral administration, the active agent is provided in dry (i.e. powder or granular) form for reconstitution with a suitable vehicle (e.g. sterile pyrogen-free water) prior to parenteral administration of the reconstituted composition.

The pharmaceutical compositions can be prepared, packaged, or sold in the form of a sterile injectable aqueous or oily suspension or solution. This suspension or solution can be formulated according to the known art, and can comprise, in addition to the active agent, additional ingredients such as the dispersing agents, wetting agents, or suspending agents described herein. Such sterile injectable formulations can be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active agent in microcrystalline form, in a liposomal preparation, or as a component of a biodegradable polymer systems. Compositions for sustained release or implantation can comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active agent, although the concentration of the active agent can be as high as the solubility limit of the active agent in the solvent. Formulations for topical administration can further comprise one or more of the additional ingredients described herein.

A pharmaceutical composition of the invention can be prepared, packaged, or sold in a formulation suitable for pulmonary administration via the buccal cavity. Such a formulation can comprise dry particles which comprise the active agent and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant can be directed to disperse the powder or using a self-propelling solvent/powder-dispensing container such as a device comprising the active agent dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant can constitute 50 to 99.9% (w/w) of the composition, and the active agent can constitute 0.1 to 20% (w/w) of the composition. The propellant can further comprise additional ingredients such as a liquid non-ionic or solid anionic surfactant or a solid diluent (preferably having a particle size of the same order as particles comprising the active agent).

Pharmaceutical compositions of the invention formulated for pulmonary delivery can also provide the active agent in the form of droplets of a solution or suspension. Such formulations can be prepared, packaged, or sold as aqueous or dilute alcoholic solutions or suspensions, optionally sterile, comprising the active agent, and can conveniently be administered using any nebulization or atomization device. Such formulations can further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active agent and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active agent, and can further comprise one or more of the additional ingredients described herein.

A pharmaceutical composition of the invention can be prepared, packaged, or sold in a formulation suitable for buccal administration. Such formulations may, for example, be in the form of tablets or lozenges made using conventional methods, and may, for example, 0.1 to 20% (w/w) active agent, the balance comprising an orally dissolvable or degradable composition and, optionally, one or more of the additional ingredients described herein. Alternately, formulations suitable for buccal administration can comprise a powder or an aerosolized or atomized solution or suspension comprising the active agent. Such powdered, aerosolized, or aerosolized formulations, when dispersed, preferably have an average particle or droplet size in the range from about 0.1 to about 200 nanometers, and can further comprise one or more of the additional ingredients described herein.

A pharmaceutical composition of the invention can be prepared, packaged, or sold in a formulation suitable for ophthalmic administration. Such formulations may, for example, be in the form of eye drops including, for example, a 0.1-1.0% (w/w) solution or suspension of the active agent in an aqueous or oily liquid carrier. Such drops can further comprise buffering agents, salts, or one or more other of the additional ingredients described herein. Other ophthalmalmically-administrable formulations which are useful include those which comprise the active agent in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; anti-fungal agents; stabilizing agents; and pharmaceutically acceptable polymeric or hydrophobic materials. Other "additional ingredients" which can be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

The relative amounts of the active agent, the pharmaceutically acceptable carrier, and any additional ingredients in a pharmaceutical composition of the invention will vary, depending upon the identity, size, and the type and severity of condition of the subject treated and further depending upon the route by which the composition is to be administered. By way of example, the composition can comprise between 0.1% and 100% (w/w) active agent.

Typically dosages of the active agent which can be administered to an animal, preferably a human, range in amount from 1 microgram to about 100 grams per kilogram of body weight of the animal. While the precise dosage administered will vary depending upon any number of factors, including but not limited to, the type of animal and type of disease state being treated, the age of the animal and the route of administration. Preferably, the dosage of the active agent will vary from about 1 milligram to about 10 g per kilogram of body weight of the animal. More preferably, the dosage will vary from about 10 milligram to about 1 gram per kilogram of body weight of the animal. Alternatively, the dosage can be determined in units of square meters of the body surface of an animal (i.e. milligrams or kilograms per square meter, mg/m$^2$ or kg/m$^2$). Preferably, this dosage will vary from about 0.1 milligram to about 5 grams per square meter of body surface of the animal. More preferably, the dosage will vary from about 1 milligram to about 1 gram per square meter of body surface of the animal.

The active agent can be administered to an animal as frequently as several times daily, or it can be administered less frequently, such as once a day, once a week, once every two weeks, once a month, or even lees frequently, such as once every several months or even once a year or less. The frequency of the dose is determinable by the skilled artisan and depends upon various factors including, but not limited to, the type and severity of the disease being treated, the type and age of the animal, etc.

The invention is now described with reference to the following Examples. These Examples are provided for the purpose of illustration only and the invention is not limited to these Examples, but rather encompasses all variations which are evident as a result of the teaching provided herein.

EXAMPLES

Unless otherwise stated, all reactions were conducted in the presence of an inert atmosphere (e.g. argon or nitrogen). All solvents were reagent grade (e.g. distilled solvents, chromatography solvents, and reaction work-up solvents) or HPLC grade (i.e. reaction solvents). Anhydrous diethyl ether and tetrahydrofuran (THF) were distilled from sodium and benzophenone. The boiling point range of the hexane used was 38-55° C. Methylene chloride ($CH_2Cl_2$), benzene, toluene, and N,N-dimethyl formamide (DMF) were distilled from calcium hydride ($CaH_2$). Organic acids and bases were reagent grade. Triethylamine ($Et_3N$), diisopropylethylamine (DIPEA), morpholine, and N-methylmorpholine (NMM) were distilled from calcium hydride ($CaH_2$). All other reagents, including dimethylaminophenol and diethyl 1,3-acetonedicarboxylate, were the highest purity commercial available. Analytical thin-layer chromatography (TLC) was performed using EM Separations Tech./Merck silica gel (60-F254) plates (0.25 millimeter) pre-coated with a fluorescent indicator. Visualization was effected using ultraviolet light (254 nanometers), phosphomolybdic acid (7% w/v) in 95% ethanol. Melting points (mp) were determined using a Thomas-Hoover capillary melting point apparatus and are reported without correction. Proton and carbon magnetic resonance spectra ($^1$H— and $^{13}$C-NMR, respectively) were recorded on a Bruker AM-500 (500 MHz) Fourier transform spectrometer, and chemical shifts were expressed in parts per million (ppm) relative to $CHCl_3$ as an internal reference (7.24 ppm for $^1$H and 77.0 for C). Multiplicities are designated as singlet (s), doublet (d), doublet of doublets (dd), doublet of triplets (dt), triplet (t), quartet (q) multiplet (m), and broad singlet (s). Infrared spectra (IR) were obtained using a Perkin-Elmer Model 1600 FT-IR spectrophotometer. Absorptions are reported in wave number ($cm^{-1}$). Optical rotations (in degrees) were measured using a Perkin-Elmer Model 341 polarimeter. High resolution mass spectra (HRMS) were obtained using either a VG 70-70HS, or a Micromass AutoSpect. Elemental Analyses were performed using a Perkin-Elmer 2400 Series II CHNS/O Analyzer. Flash column chromatography was performed using Merck silica gel 60 (240-400 mesh) using the solvent systems indicated for individual experiments.

Example 1

Synthesis of a Deoxo-Proline Side Chain Moiety and Coupling to a Didemnin Macrocycle An amino methylene single bond was used to replace the amide bond between D-leucine and L-proline in the side chain of didemnin B. Synthetically, the amino methylene bond was prepared by reductive amination, as described (Abdel-Magid et al., 1990, Tetrahedron Lett. 31:5595-5598; Abdel-Magid et al., 1990, Synlett. 537-539).

Figure 3:
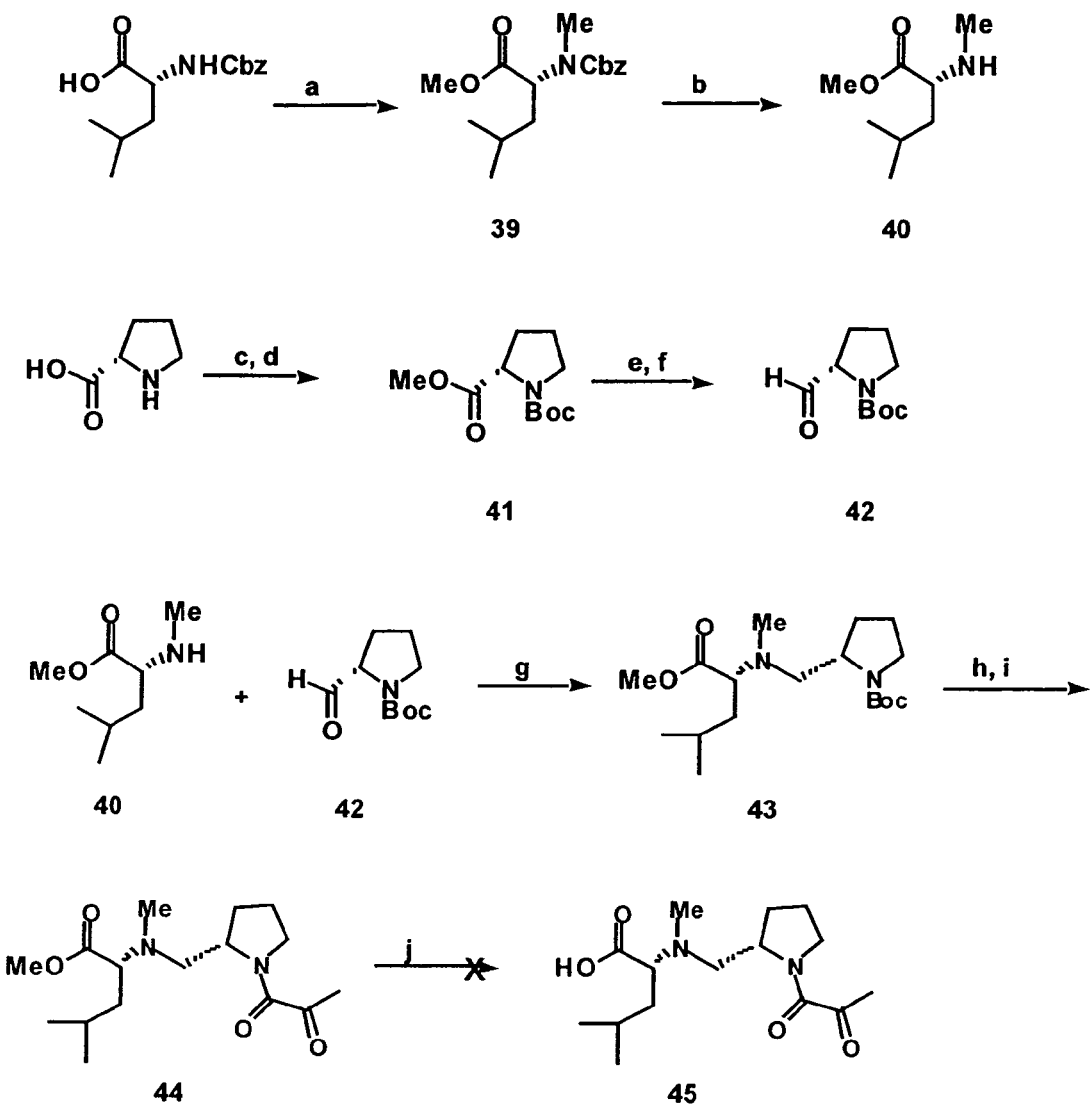

In a first synthetic method, exhaustive methylation of Cbz-D-leucine was performed using dimethylsulfate, as illustrated in FIG. 3. The Cbz group was removed using hydrogenolysis to yield dimethylated D-leucine free amine (Compound 40). The amine was used in reductive amination without purification. Commercially available L-proline was first esterified using $SOCl_2$ in MeOH, and its amino group was subsequently protected using $Boc_2O$. After purification, the ester function was reduced to an aldehyde in two steps. $NaBH_4$ was combined with LiCl to generate $LiBH_4$ in situ, and this compound was used to reduce the ester to the corresponding alcohol. Oxidation with $SO_3$.pyridine reagent gave the aldehyde, designated compound 42, in good yield. Reduction of the ester to the aldehyde in one step using DIBAL could be performed, but depended on the freshness of the reducing reagent and was not very reproducible. Reductive amination between the aldehyde designated compound 40 and the free amine (compound 42) yielded compound 43. The Boc group of compound 43 was removed using TFA/$CH_2Cl_2$. The resulting free amine was coupled with pyruvic acid using BOP to yield the protected Ψ($CH_2NH$) side chain designated compound 44.

The next step was hydrolysis of the methyl ester of compound 44. But this step was proved to be nontrivial. Perhaps owing to steric hindrance, the methyl ester was difficult to cleave using 2 equivalents of LiOH.$H_2O$ in THF/$H_2O$. When the amount of LiOH.$H_2O$ was increased to 10 equivalents, the methyl ester appeared to hydrolyze, since the mass spectrum of the reaction mixture did show the acid peak. But the acid was so hydrophilic and buried inside the excess inorganic salts, that it could not be extracted by any organic solvent. We also tried to precipitate the acid using ether but only precipitated the inorganic salts. On account of this purification problem, we decided not to use the methyl ester to protect the acid. We needed a protective group which could survive all the synthetic steps but did not require aqueous conditions for its removal. The benzyl group was found to serve this purpose well.

Figure 4:
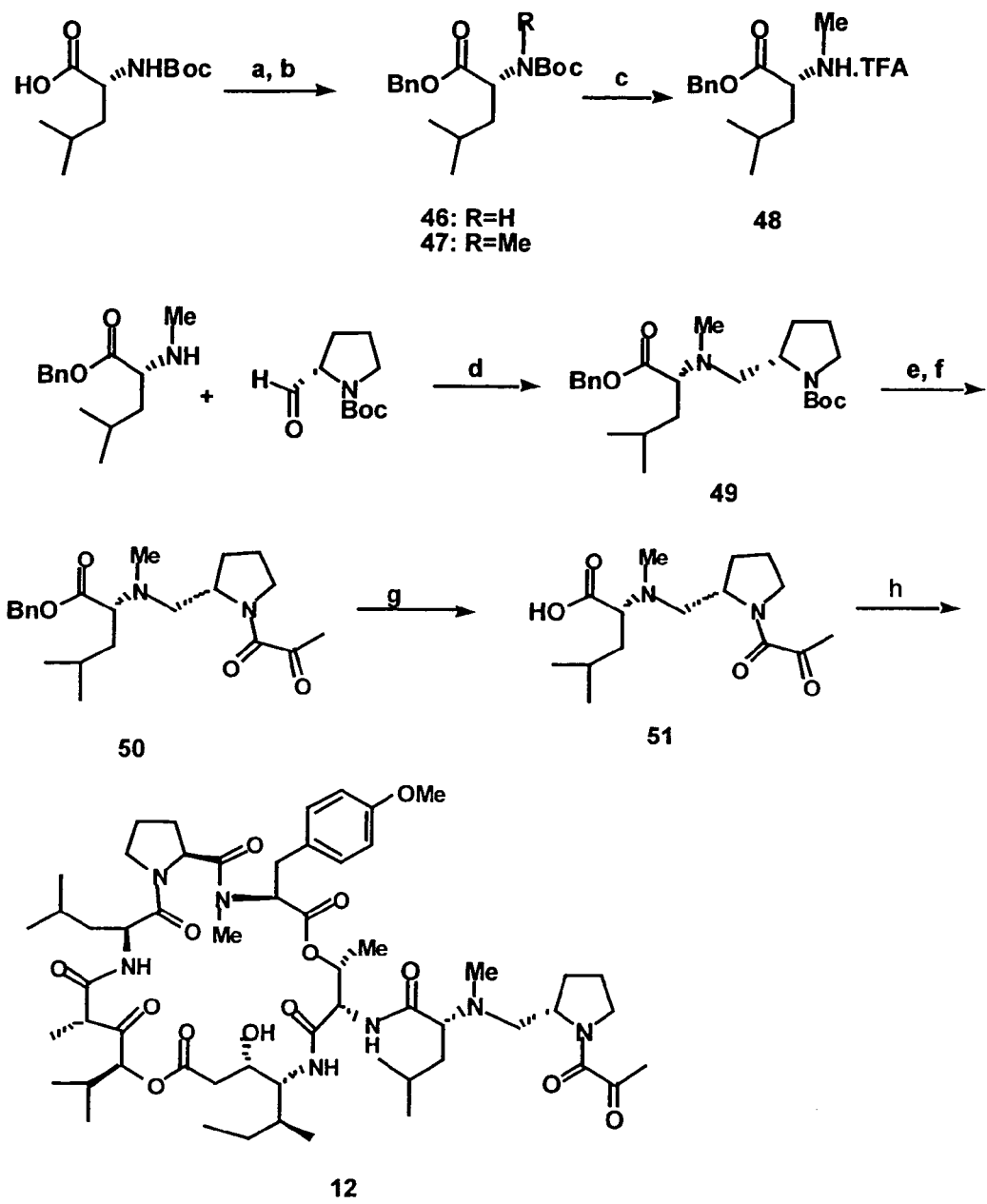

The synthetic procedure was modified as indicated in FIG. 4. In order to be compatible with the benzyl ester, the leucine amino group was protected by Boc instead of Cbz. Selective methylation of the amino group gave the acid designated compound 46. The free acid was benzylated to yield the desired benzyl ester, compound 47. The Boc protecting group was removed using TFA. The resulting amine (compound 48) was condensed with protected prolinal by reductive amination. Removal of the Boc protecting group and subsequent coupling with pyruvic acid yielded compound 50. Hydrogenolysis was used to remove the benzyl group and yielded the desired Ψ(CH$_2$NH) side chain, in the form of the free acid (compound 51). Coupling of the free acid side chain with a didenmin macrocycle gave the desired deoxo-proline didemnin analog designated compound 12.

Figure 5:
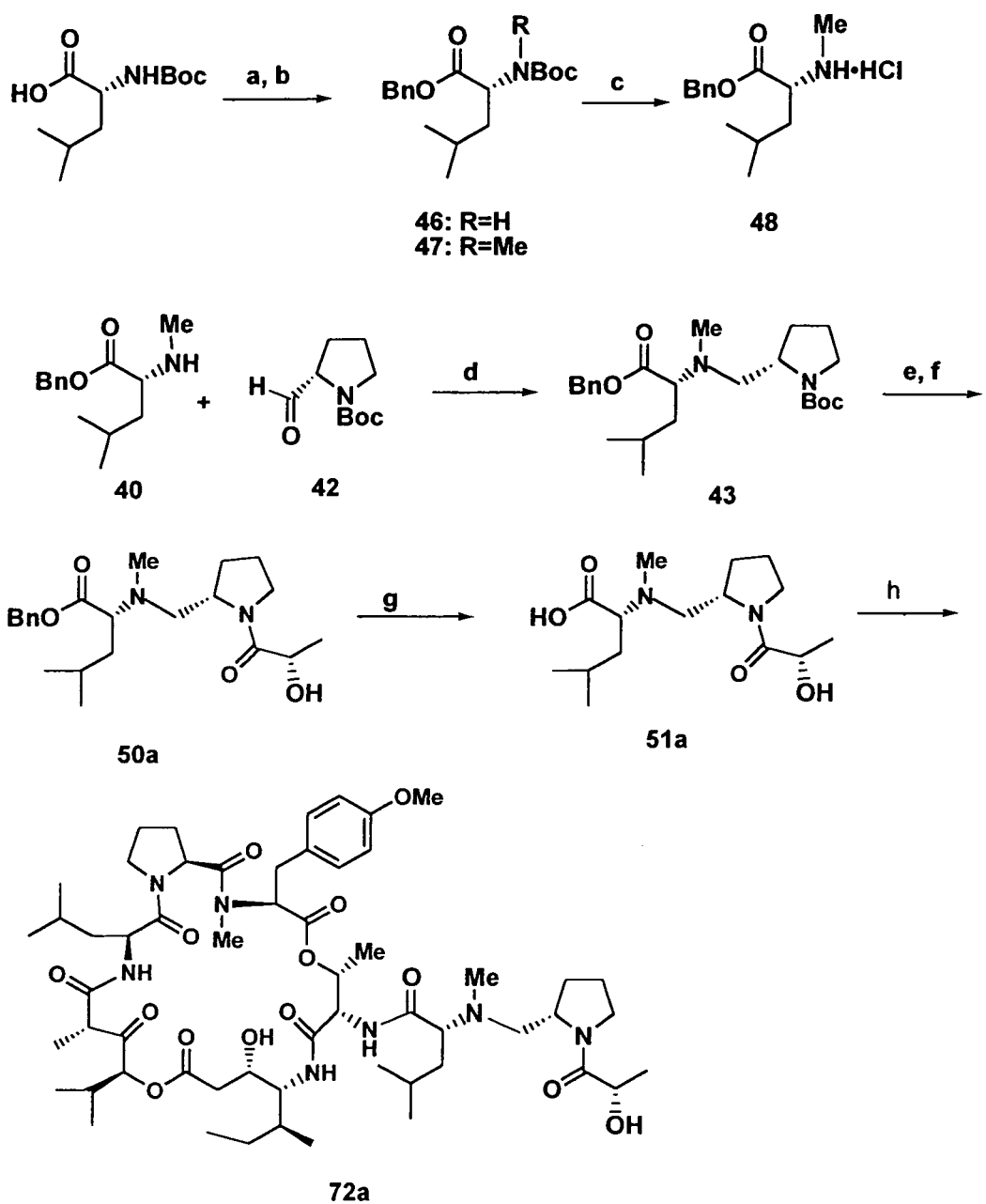
FIG. 5 depicts a method of making deoxo-proline-containing side chain moieties for tamandarin or didemnin analogs.

A second deoxo-proline didemnin analog (designated compound 72a) was synthesized using a similar synthetic strategy, as illustrated in FIG. 5 and described in detail as follows.

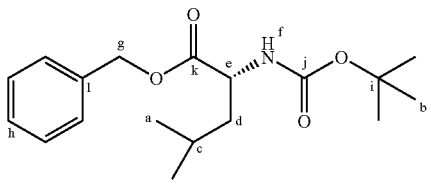

Benzyl N-Boc D-leucinate (Compound 46)

A solution of N-Boc-D-leucine (1.0 gram, 4.1 millimoles) in 20 milliliters of DMF was cooled to 0° C. Finely powdered Li$_2$CO$_3$ (1.5 grams, 20.5 millimoles) was added, followed by the addition of benzyl bromide (2.43 milliliters, 20.5 millimoles). The reaction mixture was stirred for 6 hours and monitored by TLC. When the reaction was complete, the reaction mixture was diluted with H$_2$O and extracted with EtOAc three times. The EtOAc extracts were combined and washed with brine. DMF was removed in vacuo. The crude mixture was purified with column chromatography eluting with 20% acetone/hexane to afford 46 in 78% yield. The following analytical data were obtained for compound 46: R$_f$ 0.60 (40% acetone/hexane); $[\alpha]_D^{25}$+16 (c=1.0, CHCl$_3$); $^1$H NMR (500 MHz, CDC$_3$) δ H$_a$) 0.92 (m, 6H), H$_b$) 1.48 (s, 9H), H$_c$) 1.50-1.59 (m, 1H), H$_d$) 1.60-1.69 (dd, 2H), H$_e$) 4.36 (m, 1H), H$_f$) 4.90 (d, 1H), H$_g$) 5.11-5.20 (m, 2H), H$_h$) 7.33 (m, 5H); $^{13}$C NMR (125 MHz, CDCl$_3$) δC$_a$) 21.8, C$_a$') 22.7, C$_c$) 24.7, C$_b$) 28.2, C$_d$) 41.6, C$_e$) 52.1, C$_g$) 66.7, C$_i$) 79.6, C$_h$) 128.0, 128.2, 128.4, C$_j$) 135.5, C$_j$) 155.3, C$_k$) 173.2; IR (neat) 3367 (br), 2958 (s), 1732 (s), 1715 (s), 1500 (s), 1455 (m), 1366 (w), 1120 (m) cm$^{-1}$; HRMS m/z calculated for C$_{11}$H$_{23}$N$_4$O$_2$ (M+H) 322.2017, found 322.2018.

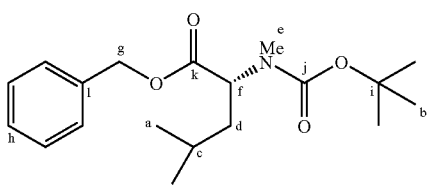

N-Boc N-Methyl benzyl D-leucinate (Compound 47)

A solution of compound 46 (1.2 grams, 3.74 millimoles) in 200 milliliters of THF was cooled to 0° C. NaHMDS (1 molar in THF; 5.6 milliliters, 5.6 millimoles) was added, followed by the addition of methyl iodide (1.0 milliliter, 18.7 millimoles). The reaction mixture was stirred overnight and monitored by TLC. When the reaction was complete, the reaction mixture was diluted with ether. The organic layer was washed with 5% HCl, 5% NaHCO$_3$, and brine. The resulting solution was dried over Na$_2$SO$_4$ and concentrated. The crude mixture was purified by column chromatography, eluting with 20% acetone/hexane to afford 47 in 71% yield. The following analytical data were obtained for compound 47: R$_f$ 0.55 (30% Acetone/Hexane); $[\alpha]_D^{25}$+20.4 (c=1.2, CHCl$_3$); $^1$H NMR (500 MHz, CDCl$_3$) δ H$_a$) 0.85-0.90 (m, 6H), H$_c$) & H$_d$) 1.35-1.65 (m, 3H), H$_b$) 1.45 (s, 9H), H$_e$) 2.75 (d, 3H), H$_f$) 4.53-4.58 & 4.81-4.88 (rm, 1H), H$_g$) 5.10 (s, 2H), H$_h$) 7.15-7.28 (m, 5H); $^{13}$C NMR (125 MHz, CDCl$_3$) δ C$_a$) 22.0 and 23.5, C$_c$) 25.8, C$_b$) 29.0, C$_d$) 31.0, C$_e$) 38.0, C$_f$) 57.0, C$_g$) 66.1, C$_i$) 80.2, C$_h$) 128.0, 128.2, 128.4, Cl) 136.5, C$_j$) 156.3, C$_k$) 173.2; IR (neat) 2958.3 (m), 1742.7 (s), 1696.8 (s), 1455.6 (s), 1390.7 (s), 1366.6 (s), 1323.5 (s), 1151.3 (s) cm$^{-1}$; HRMS m/z calculated for C$_{11}$H$_{23}$N$_4$O$_2$ (M+H) 336.2174, found 336.2178.

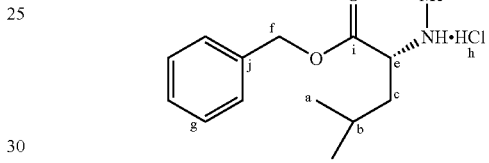

Benzyl N-Methyl D-leucinate hydrochloride salt (Compound 48)

Compound 47 (0.1 gram) was dissolved in HCl.dioxane (5 milliliters) and stirred at room temperature. When the reaction was completed, the solvent was removed in vacuo. Toluene was added twice and concentrated. The residue was dried under reduced pressure overnight to afford the desired HCl salt (compound 48) in 98%. The following analytical data were obtained for compound 48: R$_f$: baseline (10% MeOH/CH$_2$Cl$_2$); $[\alpha]_D^{25}$+48.5 (c=0.2, CHCl$_3$); $^1$H NMR (500 MHz, CDCl$_3$) δ H$_a$) 0.91 (d, 6H), H$_b$) 1.75 (m, 1H) H$_c$) 1.90-1.95 (dd, 2H), H$_d$) 2.71 (s, 3H), H$_e$) 3.83 (t, 1H), H$_f$) 5.20-5.30 (rm, 2H), H$_g$) 7.35-7.40 (m, 5H), H$_h$) 9.85 & 10.15 (br, 2H); $^{13}$C NMR (125 MHz, CDCl$_3$) δ C$_a$) 21.8, and 23.4, Cc) 25.8, C$_b$) 31.9, C$_d$) 38.2, C$_e$) 60.1, C$_f$) 68.8, C$_g$) 128.4, 128.6, 128.8, C$_j$) 134.6, C$_i$) 168.2; IR (neat) 2958.3 (m), 1742 (s), 1696 (s), 1455 (s), 1390 (s), 1366 (s), 1323 (s), 1151 (s) cm$^{-1}$; HRMS m/z calculated for C$_{11}$H$_{23}$N$_4$O$_2$ (M+H) 336.2174, found 336.2178.

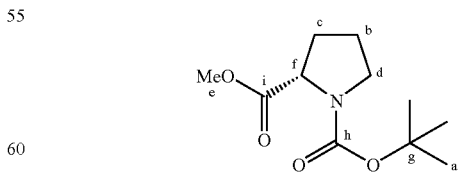

Methyl N-Boc L-Prolinate (Compound 41)

Commercially available N-Boc-L-proline (5.0 grams, 23.2 millimoles) was dissolved in acetone (200 milliliters). K$_2$CO$_3$ (3.8 grams, 27.84 millimoles) was added at 0° C., followed by the addition of MeI (2.9 milliliters, 46.4 millimoles). The reaction mixture was stirred overnight. The reaction was quenched with 5% NaHCO$_3$ solution and extracted with ether. The combined ether layers were washed with 5% HCl and brine, and concentrated to afford the crude product (compound 41) in 91% yield. This compound was purified by column chromatography eluting with 20% acetone/hexane. The following analytical data were obtained for compound 41: R$_f$ 0.4 (30% acetone/hexane); [α]$_D^{25}$–61.2 (c=0.8, CHCl$_3$); $^1$H NMR (500 MHz, CDCl$_3$) δ H$_a$) 1.45 (s, 9H), H$_b$) 1.98 (dd, 2H) H$_c$) 1.88 & 2.22 (m, rm, 2H), H$_d$) 3.42-3.58 (m, 2H), H$_e$) 3.74 (s, 3H), H$_f$) 4.24 & 4.35 (rm, 1H); $^{13}$C NMR (125 MHz, CDCl$_3$) δ C$_b$) 24.2, and 24.4, Ca) 28.3, C$_c$) 31.6 and 31.8, C$_d$) 47.3, C$_f$) 52.1, C$_e$) 59.7, C$_g$) 80.1, C$_h$) 153.8, C$_i$) 174.0; IR (neat) 2975 (m), 1749 (s), 1700 (s), 1396 (s), 1365 (s), 1200 (s), 1161 (s), 1151 (s); HRMS m/z calculated for C$_{11}$H$_{23}$N$_4$O$_2$ (M+H) 230.1391, found 230.1389.

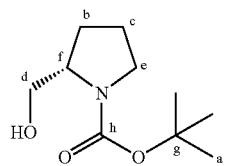

N-Boc L-Prolinol (Compound 41*a*)

Compound 41 was dissolved in 200 milliliters THF/EtOH (1:1). LiCl (1.8 grams, 32.7 millimoles) and NaBH$_4$ (1.2 grams, 32.7 millimoles) was added in portions at 0° C. The reaction mixture was stirred overnight and monitored by TLC; more LiCi and NaBH$_4$ were added during the operation. When the reaction was complete, the white solid was collected and washed with ether. The solvent was removed using a rotary evaporator. The residue was neutralized to pH 4 and then extracted twice with EtOAc. The EtOAc extracts were combined, washed with brine, dried, and concentrated. The crude product was purified by column chromatography eluting with 10% acetone/hexane to afford the desired alcohol (compound 41*a*) in 83% yield. The following analytical data were obtained for compound 41*a*: R$_f$ 0.30 (30% Acetone/Hexane); [α]$_D^{25}$–60.0 (c=0.8, CHCl$_3$); $^1$H NMR (500 MHz, CDCl$_3$) δ H$_a$) 1.48 (s, 9H), H$_b$) 1.60 & 2.05 (rm, 2H) H$_c$) 1.83-1.98 (dd, 2H), H$_d$) 3.35 & 3.45 (rm, 2H), H$_e$) 3.61-3.70 (m, 2H), H$_f$) 4.03 (m, 1H); $^{13}$C NMR (125 MHz, CDCl$_3$) δ C$_c$) 23.8, Ca) 28.4, C$_b$) 28.9, C$_f$) 47.3, C$_e$) 59.9, C$_d$) 67.3, C$_g$) 80.0, C$_h$) 156.8; IR (neat) 3424 (br), 2973 (s), 2877 (s), 1695 (s), 1670 (s), 1477 (s), 1406 (s), 1366.2 (s); HRMS m/z calculated for C$_{11}$H$_{23}$N$_4$O$_2$ (M+H) 202.1443, found 202.1449.

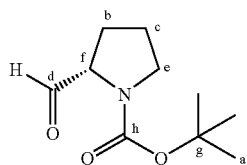

N-Boc L-prolinal (compound 42)

A solution of compound 41*a* (2.0 grams, 9.9 millimoles) and Et$_3$N in 200 milliliters of CH$_2$Cl$_2$ was cooled to –78° C. SO$_3$.pyridine complex (4.7 grams, 29.7 millimoles) in DMSO (30 milliliters) was added to the previous solution. The reaction mixture was warmed to room temperature, stirred overnight, and monitored by TLC. When the reaction was complete, the reaction mixture was diluted with ether. The organic layer was washed with 5% HCl, 5% NaHCO$_3$, and brine. The resulting solution was dried over Na$_2$SO$_4$ and concentrated. The crude mixture was purified with a short column to afford the desired aldehyde (compound 42) in 81% yield. The following analytical data were obtained for compound 42: R$_f$ 0.55 (30% Acetone/Hexane); [α]$_D^{25}$+20.4° (c=1.2, CHCl$_3$); $^1$H NMR (500 MHz, CDCl$_3$)δ H$_a$) 1.45 (s, 9H), H$_b$) 1.75-1.90 (m, 2H), H$_c$) 1.90-2.15 (m, 2H), H$_d$) 3.20-3.50 (t, 2H), H$_e$) 3.90-4.20 (d, 1H), H$_f$) 9.72 (d, 1H); $^{13}$C NMR (125 MHz, CDCl$_3$) δ C$_b$)24.0, Cc) 27.3, C$_a$) 28.9, C$_d$) 47.5, C$_e$) 65.5, Cg) 80.1, C$_h$) 154.2, C$_f$) 200.1.

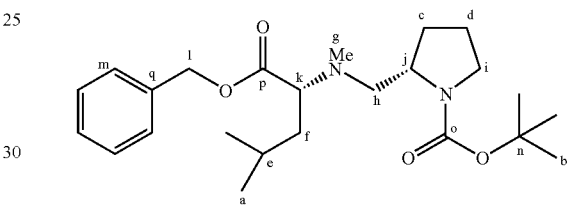

N-Boc-pro y(NHCH$_2$)
N-Methyl-Benzyl-D-Leucinate (compound 43)

Compound 42 (0.1 gram, 0.5 millimoles) was dissolved in CH$_2$Cl$_2$ (8 milliliters), and free amine 48 (0.15 gram, 0.55 millimoles) was added with efficient stirring. At 0° C., AcOH (0.02 milliliters, 0.3 millimoles) was added as a catalyst and stirred for 10 minutes before NaBH(OAc)3 (0.13 gram, 0.6 millimoles) was added to the reaction mixture. The reaction mixture was stirred at room temperature and monitored by TLC. When the reaction was complete, the mixture was diluted with CH$_2$Cl$_2$. The excess reagent was quenched by dropwise addition of saturated NH$_4$Cl solution. The organic layer was washed with 5% HCl, 5% NaHCO$_3$, and brine, dried, and concentrated. The crude product was purified by flash chromatography, eluting with 20% EtOAc/petroleum ether to afford the desired amine (compound 43). The following analytical data were obtained for compound 43: R$_f$ 0.50 (30% Acetone/Hexane); [α]$_D^{25}$ –44.0 (c=1.1, CHCl$_3$); $^1$H NMR (500 MHz, CDCl$_3$) δ H$_a$) 0.92 (m, 6H), H$_b$) 1.45 (s, 9H), H$_c$), H$_d$) & H$_e$) 1.50-1.90 (m, 5H), H$_f$) & H$_g$) 2.3-2.45 (m, 5H), H$_{h1}$) 2.22-2.90 (m, 1H), H$_2$) & H$_i$) 3.25-3.4 (m, 3H), H$_j$) & H$_k$) 3.70-3.95 (m, 2H), H$_l$) 5.35 (m, 5H), H$_m$) 7.30 (m, 5H); $^{13}$C NMR (125 MHz, CDCl$_3$) δ C$_a$) 22.2, C$_d$) 23.4, C$_c$) 25.6, C$_b$) 28.4, C$_e$) 28.8, C$_g$) 36.6, C$_f$) 38.4, C$_h$) 46.2, C$_i$) 56.1, C$_j$) 58.5, C$_l$) 56.2, C$_k$) 66.0, C$_n$) 79.6, C$_m$) 128.2, C$_q$) 136.2, C$_o$) 154.1, C$_p$) 174.2; IR (neat) 2955 (s), 2868 (s), 1730 (s), 1693 (s), 1455 (s), 1392 (s), 1364 (s), 1170 (s) cm$^{-1}$; HRMS m/z calculated for C$_{24}$H$_{38}$N$_2$O$_4$ (M+H) 419.2910, found 419.2897.

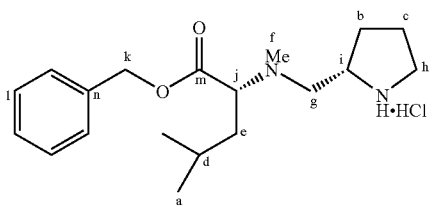

L-Pro Ψ(NHCH$_2$) N-Methyl-Benzyl-D-Leucinate Hydrochloride salt (compound 44).

Compound 43 (0.1 gram) was dissolved in HCl-dioxane (5 milliliters), and the solution was stirred at room temperature. When the reaction was completed, all solvent was removed in vacuo. Toluene was added twice and concentrated. The residue was dried under reduced pressure overnight to afford the desired HCl salt (compound 44) in 98%. The following analytical data were obtained for compound 44: R$_f$ baseline (60% EA/PE); [α]$_D^{25}$ +15.3 (c=0.6, CHCl$_3$); $^1$H NMR (500 MHz, CDCl$_3$) δ H$_a$) 0.91-1.10 (d, 6H), H$_b$), H$_c$) & H$_d$) 1.68-2.30 (m, 5H), H$_e$) 2.83 (dd, 2H), H$_f$) 3.12 (s, 3H), H$_g$) & H$_h$) 3.31-3.65 (m, 4H), H$_i$) & H$_j$) 4.11-4.30 (m, 2H), H$_k$) 5.28 (s, 2H), H$_l$) 7.40 (m, 5H); $^{13}$C NMR (125 MHz, CDCl$_3$) δ C$_c$) 20.8, C$_b$) 23.5, C$_a$) 25.9, C$_d$) 26.1, C$_e$) 36.2, C$_f$) 46.2, C$_g$) 55.8, C$_h$) 61.6, C$_i$) 64.2, C$_j$) 67.0, C$_k$) 68.2, C$_l$) 125.0, 128.0, 128.8, 128.9 & 134.1, C$_n$) 137.9, C$_m$) 167.0; IR (neat) 2954 (s), 2360 (s), 2338 (s), 1740 (s), 1455 (s), 1389 (s), 1197 (s), 1141 (s); cm$^{-1}$; HRMS m/z calculated for C$_{19}$H$_{30}$N$_2$O$_2$ (M+H) 319.2386, found 319.2392.

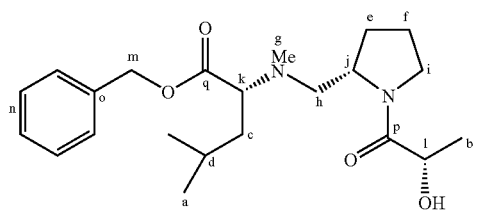

L-Lactyl-Pro Ψ(NHCH$_2$) N-Methyl-Benzyl-D-Leucinate (compound 50a)

Compound 44 (20 milligrams, 0.063 millimoles) was dissolved in CH$_2$Cl$_2$ (0.5 milliliters), and lactic acid (5.55 milligrams, 0.063 millimoles) was added at 0° C., followed by the addition of BOP (28 milligrams, 0.063 millimoles and NMM (0.035 milliliters, 0.31 millimoles). The reaction mixture was stirred at 0° C. and monitored by TLC. When the reaction was completed, the reaction mixture was diluted with ether. The organic layer was washed with 5% HCl, 5% NaHCO$_3$, and brine. The resulting solution was dried over Na$_2$SO$_4$ and concentrated. The crude mixture was purified by column chromatography, eluting with 30% acetone/hexane to afford compound 50a in 61% yield. The following analytical data were obtained for compound 50a: R$_f$ 0.50 (50% Acetone/Hexane); [α]$_D^{25}$ +21.0 (c=0.2, CHCl$_3$); $^1$H NMR (500 MHz, CDCl$_3$) δ H$_a$) 0.82-0.92 (d, 6H), H$_b$) 1.20 (d, 3H), H$_c$) 1.45-1.66 (m, 2H), H$_d$) 1.66-1.72 (m, 1H), H$_e$) & H$_f$) 1.76-1.90 (m, 4H), H$_g$) & H$_h$) 2.25-2.45 (m, 5H), H$_i$), H$_j$) & H$_k$) 3.19-3.85 (m, 4H), H$_l$) 4.10-4.21 (rm, 1H), H$_m$) 5.05-5.18 (s, 2H), H$_n$) 7.12-7.38 (m, 5H); $^{13}$C NMR (125 MHz, CDCl$_3$) δ C$_a$) 22.0, C$_c$) 22.8, C$_d$) 24.2, C$_e$) 24.8, C$_b$) 25.4, C$_f$) 28.1, C$_g$) 37.8, C$_h$) 38.6, C$_j$) 45.8, C$_i$) 46.2, C$_k$) 56.0, C$_l$) 56.8, C$_m$) 66.0, C$_n$) 128.8, C$_o$) 136.1, C$_p$) 173.8, C$_q$) 174.1; IR (neat), 3415 (br), 2955 (s), 2869 (m), 1729 (s), 1638 (s), 1455 (m), 1379 (m), 1366 (m), 1147 (m), 1126 (m); HRMS m/z calculated for C$_{22}$H$_{34}$N$_2$O$_4$ (M+Na) 413.2416, found 413.2423.

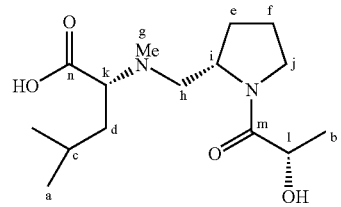

N-Methyl-leu Ψ(NHCH$_2$) lac-pro acid (compound 51a)

Compound 50a (20 milligrams, 0.063 millimoles) was dissolved in 0.5 milliliters MeOH/EtOAc (1:1). The mixture was added to a solution of MeOH and EtOH (1:1) containing Pd/C catalyst (10 milligrams). The reaction mixture was shaken in a Parr hydrogenator under H$_2$ (40 pounds per square inch, gauge) and monitored by TLC. When the reaction was completed, the catalyst was removed by filtration. The remaining solution was concentrated in vacuo. The crude product (compound 51a) was used directly in the next step. The following analytical data were obtained for compound 51a: R$_f$ 0.20 (10% MeOH/CH$_2$Cl$_2$); [α]$_D^{25}$ +65.0 (c=0.2, CHCl$_3$); $^1$H NMR (500 MHz, CDCl$_3$) δ H$_a$) 0.82-0.92 (d, 6H), H$_b$) 1.34 (d, 3H), H$_c$) 1.45-1.55 (m, 1H), H$_d$) 1.78-1.91 (m, 2H), H$_e$) 1.91-2.0 (m, 2H), H$_f$) 2.0-2.18 (m, 2H), H$_g$) 2.81 (s, 3H), H$_h$) 3.03-3.18 (d, 2H), H$_i$) 3.45-3.54 (m, 1H), H$_j$) 3.56-3.68 (t, 2H), H$_k$) 4.25-4.35 (m, 1H), H$_l$) 4.40-4.49 (m, 1H); $^{13}$C NMR (125 MHz, CDCl$_3$) δ C$_a$) 21.0, C$_b$) 22.8, C$_c$) 23.4, C$_d$) 24.8, C$_e$) 25.8, C$_f$) 29.4, C$_g$) 36.5, C$_h$) 38.6, C$_i$) 47.2, C$_j$) 55.2, C$_k$) 66.4, C$_l$) 68.2, C$_m$) 172.4, C$_n$) 176.2; IR (neat), 3336 (br), 2957 (s), 2870 (m), 1718 (m), 1627 (s), 1466 (s), 1368 (s), 1250 (m), 1197 (w), 1128 (w); HRMS m/z calculated for C$_{15}$H$_{27}$N$_2$O$_4$ (M+Na) 323.1947, found 323.1939.

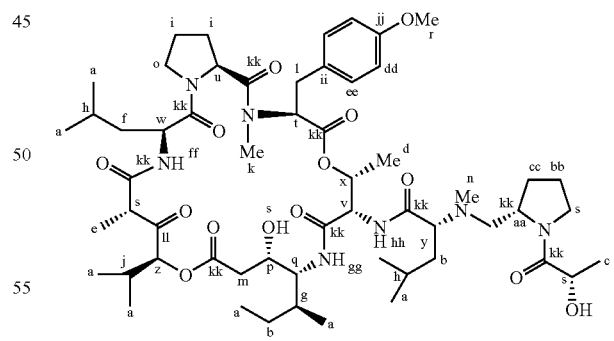

Cyclo[N—(N-3,4-didehydro-L-prolyl-N-methyl-D-leucyl)-O[[N-[(2S,3 S,4S)-4-[(3S,4R,5S)-4-amino-3-hydroxy-5-methyl-heptanoyl]oxy-3-oxo-2,5-dimethylhexanoyl]-L-leucyl]-L-prolyl-N,O-dimethyl-L-tyrosyl]-L-threonyl] (compound 72a)

The crude acid (12.5 milligrams, 0.038 millimoles) was combined with the macrocycle HCl salt (15.0 milligrams, 0.019 millimole) in CH$_2$Cl$_2$ (0.25 milliliter) at 0° C. HATU (8.2 milligrams, 0.020 millimole) and DIEA (0.026 milliliter, 4 equivalents) was added. The reaction was stirred at 0° C. overnight and monitored by TLC. When the reaction was complete, the mixture was diluted with Et$_2$O and the organic layer was washed with 5% HCl, 5% NaHCO$_3$, and brine. The resulting solution was dried over Na$_2$SO$_4$ and concentrated. The crude residue was purified by column chromatography eluting with 5% MeOH/CH$_2$Cl$_2$ to yield the desired product (compound 72a) in 72% yield. The following analytical data were obtained for compound 72a: R$_f$ 0.40 (10% MeOH/CH$_2$Cl$_2$); [α]$_D^{25}$ +81.2 (c=0.15, CHCl$_3$); $^1$H NMR (500 MHz, CDCl$_3$) δ H$_a$) 0.85-0.97 (m, 24H), H$_b$) 1.17-1.27 (m, 2H), H$_c$) 1.28-1.39 (s, 3H), H$_d$) 1.40 (d, 3H), H$_e$) 1.43 (d, 3H), H$_f$) 1.46-1.50 (m, 1H) and 1.61 (t, 1H), H$_g$) 1.68-1.73 (m, 1H), H$_h$) 1.74-1.79 (m, 1H), H$_i$) 1.82-1.88 (m, 2H), 2.02-2.08 (m, 1H) and 2.11-2.17 (m, 2H), H$_j$) 2.34-2.37 (m, 1H), H$_k$) 2.57 (s, 3H), H$_l$) 2.38 (d, 2H), H$_m$) 3.18 and 3.39 (dd, 1H), H$_n$) 2.83 (s, 3H), H$_o$) 3.37-3.57 (m, 2H), H$_p$) 3.60 (d, 1H), H$_q$) 3.70-3.73 (m, 1H), H$_r$) 3.80 (s, 3H), H$_s$) 4.05-4.14 (m, 3H) and 4.36-4.48 (m, 2H), H$_t$) 4.27 (q, 1H), H$_u$) 4.56 (dd, 1H), H$_v$) 4.65 (dd, 1H), H$_w$) 4.81 (t, 1H), H$_x$) 5.19 (d, 1H), H$_y$) 5.35 (dd, 1H), H$_z$) 5.42 (dd, 1H), H$_{aa}$) 5.61 (dd, 1H), H$_{bb}$) 5.73-5.75 (m, 1H), H$_{cc}$) 6.11 (dd, 1H), H$_{dd}$) 6.85 (d, 2H), H$_{ee}$) 7.08 (d, 2H), H$_{ff}$) 7.20 (d, 1H), H$_{gg}$) 7.54 (d, 1H), H$_{hh}$) 7.78 (d, 1H); $^{13}$C NMR (125 MHz, CDCl$_3$) δ C$_a$), C$_c$) 11.7, 14.7, 15.2, 16.3, 16.9, 18.6, 20.1 and 20.9, C$_d$) 23.3, C$_b$) 23.7, C$_b$) 24.8 and 27.2, C$_i$) 24.9, 25.0 and 33.9, C$_f$) 27.9, C$_g$) 31.2, C$_h$) 31.3, C$_j$) 33.9, C$_l$) 36.2, C$_m$) 38.7, C$_k$) 38.8, C$_n$) 41.3, C$_o$) 46.9, C$_q$) 49.46, C$_s$) 49.52, 53.0, and 67.9, C$_r$) 55.3, C$_v$) 55.4, C$_w$) 55.5, C$_u$) 57.2, C$_y$) 57.6, C$_t$) 63.9, C$_{aa}$) 65.9, C$_s$) 66.4, C$_p$) 66.5, C$_x$) 70.4, C$_z$) 81.5, C$_{dd}$) 114.1, C$_{cc}$) 124.0, C$_{bb}$) 129.1, C$_{ii}$) 130.0, C$_{ee}$) 130.3, C$_{jj}$) 158.6, C$_{kk}$) 168.6, 169.3, 170.5, 170.6, 171.3, 171.5, 172.4, 173.9, C$_{ll}$) 204.9; IR (neat) 3331 (br), 2956 (s), 2871 (m), 1732 (s), 1638.3 (br, overlap), 1543 (m), 1513 (s), 1448 (m), 1379 (m), 1247 (w), 1167 (w) cm$^{-1}$; HRMS m/z calculated for C$_{57}$H$_{91}$N$_7$O$_{14}$ (M+H) 1098.6702, found 1098.6726.

Example 2

Synthesis of a 3,4-Dehydro-Proline Side Chain Moiety and Coupling to a Didemnin Macrocycle Synthesis of the 3,4-dehydroproline unit began with trans-4-hydroxy-L-proline (compound 52), which was produced as described (Rueger et al., 1982, Can. J. Chem. 60:2918; see FIG. 6). The acid was first protected as its ethyl ester. The amino group was further protected using Boc$_2$O to yield compound 53. The hydroxyl group was mesylated using MsCl and pyridine. The mesylate (i.e., methyl sulfonate moiety of compound 53) was displaced by sodium benzene selenide with inversion of stereochemistry to yield compound 54. Oxidative elimination of the phenyl selenium group afforded the corresponding alkene (compound 55) in 73% yield.

If compound 54 was directly exposed to the basic elimination condition, two regioisomers would be generated. But oxidative elimination of compound 54 through phenyl selenium as the intermediate gave only the desired regioisomer. This regioselectivity may be due to the transition state leading to the undesired isomer has larger dipole moment with higher energy.

Hydrolysis of the ethyl ester (compound 55) yielded the free dehydroproline acid (compound 56), which was coupled with D-leucine ester to yield compound 57. Hydrolysis of the methyl ester afforded the free acid, which was coupled to the didemnin macrocycle salt using HATU to afford compound 58. The Boc protecting group was removed using HCl gas, and the HCl salt was neutralized using saturated NaHCO$_3$ solution to afford the final analog, compound 59.

The steps in this synthesis are now described in greater detail.

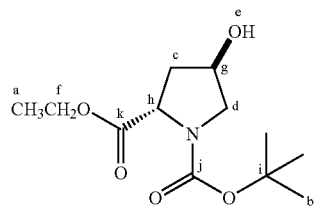

Ethyl N-Boc-trans-4-Hydroxyprolinate (compound 53). Ethyl trans-4-hydroxy prolinate hydrochloride salt (1.0 gram, 0.005 mole) was dissolved in saturated CH$_2$Cl$_2$ (10 milliliter). Et$_3$N (2.09 milliliter, 0.015 mole) was added at 0° C., followed by addition of Boc$_2$O (2.23 g, 0.01 mole). The reaction mixture was stirred overnight. When the reaction was complete, the pH was measured, and was then 8. The reaction mixture was washed with ether, and the ether layer was discarded. The aqueous layer was acidified with 1 normal KHSO$_4$ to pH 4, followed by extraction three times with ethyl acetate. The organic extracts were combined, washed with brine, dried, and concentrated. The crude mixture was purified by column chromatography, eluting with 20% acetone/hexane to affect the desired product (compound 53) in 71% yield. The following analytical data were obtained for compound 53: R$_f$ 0.50 (40% Acetone/Hexane); [α]$_D^{25}$ +71.3 (c=0.2, CHCl$_3$); $^1$H NMR (500 MHz, CDCl$_3$) δ H$_a$) 1.07-1.13 (t, 6H), H$_b$) 1.32-1.36 (m, 9H), H$_c$) 1.84-2.15 (m, dr, 2H), H$_d$) 3.23-3.49 (m, dr, 2H), H$_e$) 3.78-3.95 (br, 1H), H$_f$) 3.96-4.09 (m, 2H), H$_g$) 4.17-4.26 (m, 1H), H$_h$) 4.27-4.32 (t, 1H); $^{13}$C NMR (125 MHz, CDCl$_3$) δ C$_a$) 14.0, C$_b$) 28.1, C$_c$) 38.2, C$_d$) 54.2, C$_f$) 57.7, C$_g$) 61.0, C$_h$) 69.0, C$_i$) 80.0, C$_j$) 153.9, C$_k$) 172.6; IR (neat) 3448 (br), 2978 (s), 2935 (m), 1746 (m), 1702 (s), 1676 (s), 1477 (m), 1402(s), 1367 (m), 1339 (m) cm$^{-1}$; HRMS m/z calculated for C$_{11}$H$_{23}$N$_4$O$_2$ (M+H) 260.1497, found 260.1503.

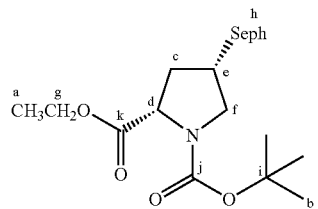

Ethyl N-Boc-cis-4-phenylselenyl-L-prolinate (compound 54). Sodium borohydride (0.15 gram, 0.004 mole) was added in small portions, at room temperature, to a solution of diphenyl diselenide (0.556 gram, 0.0018 mole) in EtOH. The mixture was stirred for about 5 minutes, until the bright yellow color disappeared. The previously prepared mesylate (1.0 gram, 0.003 mole) was added, the solution was refluxed for 2 hours, and the solvent was removed in vacuo. The residue was diluted with Et₂O (5 milliliters), and the organic layer was washed with H₂O (10 milliliters) and brine. The resulting organic layer was dried and concentrated. The crude oil was purified by column chromatography, eluting with 10% acetone/hexane to afford the product (compound 54) in 85% yield. The following analytical data were obtained for compound 54: $R_f$ 0.53 (30% Acetone/Hexane); $[\alpha]_D^{25}$ −16.4 (c=0.3, CHCl₃); ¹H NMR (500 MHz, CDCl₃) δ $H_a$) 1.21-1.24 (t, 3H), $H_b$) 1.45 (s, 9H), $H_c$) 2.05 & 2.68 (dr, 2H), $H_d$) 3.40 (m, 1H), $H_e$) 3.58 (m, 1H), $H_{f1}$) 3.95 (m, 1H), $H_{f2}$) & $H_g$) 4.10-4.28 (m, 2H), $H_h$) 7.25, 7.55 (m, 5H); ¹³C NMR (125 MHz, CDCl₃) δ $C_a$) 14.0, $C_b$) 28.2, $C_c$) 36.1, $C_d$) 39.8, $C_e$) 53.6, $C_f$) 58.8, $C_g$) 60.8, $C_i$) 80.2, $C_h$) 127.0, 128.2, 134.3, $C_j$) 152.8, $C_k$) 171.8; IR (neat) 2977.0, 1747.1, 1701.9, 1477.4, 1394.4, 1190.1, 1114.1 (m) cm⁻¹; HRMS m/z calculated for $C_{18}H_{25}NO_4Se$ (M+H) 399.0948, found 399.0957.

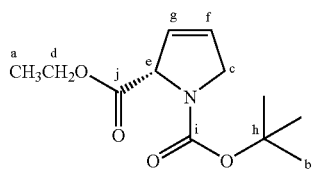

Ethyl N-Boc-3,4-Dehydro-L-prolinate (compound 55). A mixture of compound 54 (0.9 gram, 2.26 millimoles) and CH₂Cl₂ was initially cooled to 0° C. in an ice bath. Pyridine (0.27 milliliter, 3.4 millimoles) was added dropwise to this solution. A solution of 30% aqueous H₂O₂ (0.58 milliliter) was then gradually added over a 5 minute period. The reaction was stirred at room temperature for 1 hour, and then diluted with EtOAc. The organic layer was washed with 5% HCl, saturated Na₂CO₃ solution, and brine. The resulting solution was dried and concentrated. The residue was purified by column chromatography to afford the desired product (compound 55) in 73% yield. The following analytical data were obtained for compound 55: $R_f$ 0.63 (30% Acetone/Hexane); $[\alpha]_D^{25}$ −32.3 (c=0.3, CHCl₃); ¹H NMR (500 MHz, CDCl₃) δ $H_a$) 1.15-1.30 (t, 3H), $H_b$) 1.45 (s, 9H), $H_c$) & $H_d$) 4.15-4.30 (m, 4H), $H_e$) 4.98 (d, 1H), $H_f$) 5.75 (dt, 1H), $H_g$) 5.95 (dd, 1H); ¹³C NMR (125 MHz, CDCl₃) δ $C_a$) 14.1, $C_b$) 29.2, $C_c$) 53.8, $C_d$) 61.8, $C_e$) 67.0, $C_h$) 80.1, $C_f$) 125.0, $C_g$) 129.2, $C_i$) 154.0, $C_j$) 170.2; IR (neat) 3458 (br), 2979 (s), 1786 (s), 1750 (s), 1710 (s), 1448 (m), 1395 (m), 1369 (s), 1318 (s), 1258 (m), 1159 (s), 1896 (m) cm⁻¹; HRMS m/z calculated for $C_{12}H_{19}NO_4$ (M+H) 242.1392, found 242.1386.

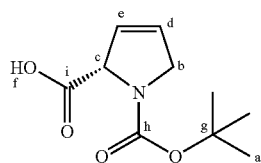

N-Boc-3,4-Dehydro-L-proline (compound 56). Ethyl ester 55 (0.18 gram, 0.8 millimole) was dissolved in THF/H₂O (1:1, 10 milliliters). LiOH.H₂O (0.33 gram, 8 millimoles) was added to the solution at 0° C. The mixture was stirred for about 6 hours and monitored by TLC. When the reaction was completed, THF was removed in vacuo. Saturated NaHCO₃ solution was added and washed with ether twice. All aqueous layers were combined and acidified to pH 4 with 1 normal KHSO₄. Ethyl acetate was used to extract the acidified aqueous solution three times. The extracts were dried and concentrated to afford the desired acid (compound 56) in 92% yield. The following analytical data were obtained for compound 56: $R_f$ 0.20 (30% acetone/hexane); $[\alpha]_D^{25}$ +8.4 (c=0.2, CHCl₃); ¹H NMR (500 MHz, CDCl₃) δ $H_a$) 1.49 (s, rm, 9H), $H_b$) 4.25 (d, 2H), $H_c$) 5.05 (d, 1H), $H_d$) 5.80 (dt, 1H), $H_e$) 6.01 (dd, 1H), $H_f$) 8.40 (br, 1H); ¹³C NMR (125 MHz, CDCl₃) δ $C_a$) 28.9, $C_b$) 53.9, $C_c$) 66.2, $C_g$) 81.8, $C_d$) 124.2, $C_e$) 129.9, $C_h$) 154.5, $C_i$) 165.3; IR (neat) 3000-3400 (br), 2957 (s), 1736 (s), 1704 (s), 1666 (s), 1400.2 (s), 1367 (m), 1177 (s), 1136 (s) cm⁻¹; HRMS m/z calculated for $C_{10}H_{15}NO_4$ (M+H) 213.1079, found 242.1086.

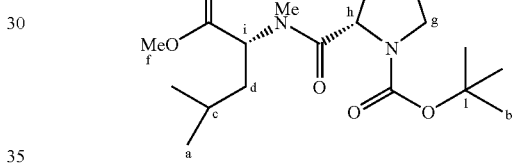

N-Boc-3,4-Dehydro-L-Prolyl-Methyl-N-Methyl-Leucinate (compound 57). Compound 56 (0.1 gram, 0.469 millimole) was dissolved in CH₂Cl₂ (5 milliliters). At 0° C., HATU (0.26 gram, 0.58 millimole) was added, followed by the addition of DIEA (0.26 milliliter, 1.88 millimoles). Finally, dimethyl D-leucine hydrochloride salt (0.09 gram, 0.469 millimole) was added to the mixture. The reaction mixture was stirred for 6 hours and monitored by TLC. When the reaction was completed, the mixture was diluted with Et₂O and the organic layer was washed with 5% HCl, 5% NaHCO3, and brine. The resulting solution was dried and concentrated. The crude residue was purified by column to afford the desired product (compound 57) in 76% yield. The following analytical data were obtained for compound 57: $R_f$ 0.32 (30% Acetone/Hexane); $[\alpha]_D^{25}$ −22.7 (c=0.4, CHCl₃); ¹H NMR (500 MHz, CDCl₃) δ $H_a$) 0.90-1.05 (d, rm, 6H), $H_b$) 1.48 (s, rm, 9H), $H_c$) & $H_d$) 1.65-1.80 (m, 3H), $H_e$) 3.05 (s, 3H), $H_f$) 3.75 (s, 3H), $H_g$) 4.20-4.35 (m, 2H), $H_h$) 5.28 (t, 1H), $H_i$) 5.40 (d, 1H), $H_j$) 5.70 (dt, 1H), $H_k$) 6.01 (dd, 1H); ¹³C NMR (125 MHz, CDCl₃) δ $C_a$) 22.0, 23.8, $C_c$) 25.2, $C_b$) 29.0, $C_d$) 37.8, $C_e$) 52.2, $C_h$) 53.8, $C_i$) 65.8, $C_l$) 80.0, $C_j$) 124.0, $C_k$) 129.2, $C_m$) 159.5, $C_n$) 171.0, $C_o$) 172.2; IR (neat) 2956 (s), 1743 (s), 1705 (s), 1667(s), 1400(s), 1366(m), 1316(w), 1258 (w), 1177 (m), 1128 (m) cm⁻¹; HRMS m/z calculated for $C_{18}H_{30}N_2O_5$ (M+H) 355.2233, found 355.2225.

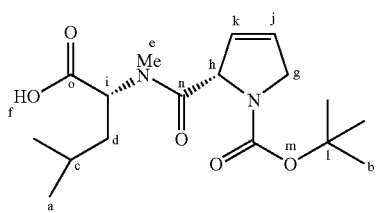

N-Boc-3,4-Dehydro-L-Prolyl-N-Methyl-Leucine (compound 57a). Compound 57 (0.13 gram, 0.37 millimole) was dissolved in THF/H$_2$O (1:1, 5 milliliters). LiOH.H$_2$O (0.15 gram, 3.7 millimoles) was added to the solution at 0° C. The mixture was stirred for about 6 hours and monitored by TLC. When the reaction was completed, THF was removed in vacuo. Saturated NaHCO$_3$ solution was added and washed with ether twice. All aqueous layers were combined and acidified to pH 4 with 1 normal KHSO$_4$. Ethyl acetate was used to extract the acidified aqueous solution three times. The extracts were dried and concentrated to afford the desired acid (compound 57a) in 92% yield. The following analytical data were obtained for compound 57a: R$_f$ 0.20 (40% Acetone/Hexane); [α]$_D^{25}$ +52.3 (c=0.2, CHCl$_3$); $^1$H NMR (500 MHz, CDCl$_3$) δ H$_a$) 0.85-1.05 (d, rm, 6H), H$_b$) 1.48 (s, rm, 9H), H$_c$) & H$_d$) 1.65-1.92 (m, 3H), H$_e$) 3.12 (s, rm, 3H), H$_f$) br, 1H, H$_g$) 4.10-4.28 (m, 2H), H$_h$) 5.15 (t, 1H), H$_i$) 5.35 (d, 1H), H$_j$) 5.70 (dt, 1H), H$_k$) 6.01 (dd, 1H); $^{13}$C NMR (125 MHz, CDCl$_3$) δ C$_a$) 23.3, 24.5, C$_c$) 25.0, C$_b$) 28.3, C$_d$) 31.5, C$_g$) 38.5, C$_e$) 53.6, C$_i$) 55.8, C$_h$) 65.2, C$_l$) 80.0, C$_j$) 124.1, C$_k$) 129.5, C$_m$) 153.8, C$_n$) 171.3, C$_o$) 175.3; IR (neat) 3300 (br), 2957 (s), 1731 (m), 1783 (s), 1667 (s), 1612 (m), 1481 (m), 1400 (s), 1367 (m), 1177 (s), 1136.7 (s) cm$^{-1}$; HRMS m/z calculated for C$_{17}$H$_{28}$N$_2$O$_5$ (M+H) 341.2076, found 341.2063.

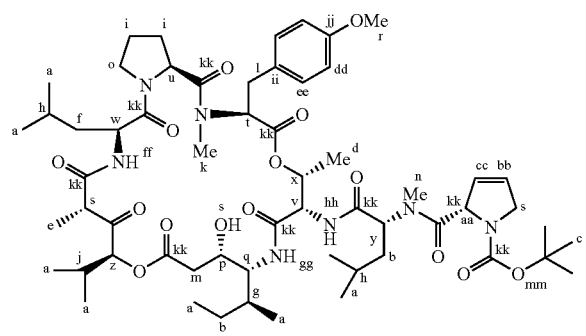

Cyclo[N—(N-Boc-3,4-dehydro-L-prolyl-N-methyl-D-leucyl)-O[[N-[(2S,3S,4S)-4[(3S,4R,5S)-4-amino-5-hydroxy-5-methyl-heptanoyl]oxy-3-oxo-2,5-dimethylhexanoyl]-L-leucyl]-L-prolyl-N,O-dimethyl-L-tyrosyl]-L-threonyl] (compound 58). The crude acid 57a (5.0 milligrams, 0.012 millimole) was combined with the macrocycle HCl salt (14.9 milligrams, 0.012 millimole) in CH$_2$Cl$_2$ (0.1 milliliter) at 0° C. HATU (48 milligrams, 0.012 millimole) and DIEA (0.048 milliliter, 0.048 millimole) was added. The reaction was stirred at 0° C. overnight and monitored by TLC. When the reaction was complete, the mixture was diluted with Et$_2$O and the organic layer was washed with 5% HCl, 5% NaHCO$_3$, and brine. The resulting solution was dried and concentrated. The crude residue was purified by column chromatography, eluting with 5% MeOH/CH$_2$Cl$_2$ to afford the desired product (compound 58) in 72% yield. The following analytical data were obtained for compound 58: R$_f$ 0.40 (10% MeOH/CH$_2$Cl$_2$); [α]$_D^{25}$ −83.2 (c=0.3, CHCl$_3$); 1H NMR (500 MHz, CDCl$_3$) δ H$_a$) 0.85-0.97 (m, 24H), H$_b$) 1.17-1.27 (m, 3H), H$_c$) 1.45 (s, 9H), H$_d$) 1.40 (d, 3H), H$_e$) 1.43 (d, 3H), H$_f$) 1.46-1.50 (m, 1H) and 1.61 (t, 1H), H$_g$) 1.68-1.73 (m, 1H), H$_h$) 1.74-1.79 (m, 1H), H$_i$) 1.82-1.88 (m, 2H), 2.02-2.08 (m, 1H) and 2.11-2.17 (m, 2H), H$_j$) 2.34-2.37 (m, 1H), H$_k$) 2.57 (s, 3H), H$_l$) 2.63 (dd, 1H) and 2.95 (d, 1H), H$_m$) 3.18 and 3.39 (dd, 1H), H$_n$) 3.23 (s, 3H), H$_o$) 3.57-3.61 (m, 2H), H$_p$) 3.33 (d, 1H), H$_q$) 3.69-3.71 (m, 1H), H$_r$) 3.80 (s, 3H), H$_s$) 4.05-4.14 (m, 2H) and 4.36-4.48 (m, 2H), H$_t$) 4.27 (q, 1H), H$_u$) 4.56 (dd, 1H), H$_v$) 4.65 (dd, 1H), H$_w$) 4.81 (t, 1H), H$_x$) 5.19 (d, 1H), H$_y$) 5.35 (dd, 1H), H$_z$) 5.42 (dd, 1H), H$_{aa}$) 5.61 (dd, 1H), H$_{bb}$) 5.73-5.75 (m, 1H), H$_{cc}$) 6.11 (dd, 1H), H$_{dd}$) 6.85 (d, 2H), H$_{ee}$) 7.08 (d, 2H), H$_{ff}$) 7.20 (d, 1H), H$_{gg}$) 7.54 (d, 1H), H$_{hh}$) 7.78 (d, 1H); $^{13}$C NMR (125 MHz, CDCl$_3$) δ C$_a$) 11.7, 14.7, 15.2, 16.3, 16.9, 18.6, 20.1 and 20.9, C$_d$) 23.3, C$_e$) 23.7, C$_a$) 24.8 and 27.2, C$_i$) 24.9, 25.0 and 33.9, C$_f$) 27.9, C$_c$) 28.6, C$_g$) 31.2, C$_h$) 31.3, C$_j$) 33.9, C$_l$) 36.2, C$_m$) 38.7, C$_k$) 38.8, C$_n$) 41.3, C$_o$) 46.9, C$_q$) 49.46, C$_s$) 49.52, 53.0, and 67.9, C$_r$) 55.3, C$_v$) 55.4, C$_w$) 55.5, C$_u$) 57.2, C$_y$) 57.6, C$_t$) 63.9, C$_{aa}$) 65.9, C$_p$) 66.5, C$_x$) 70.4, C$_z$) 81.5, C$_z$) 81.7, C$_{dd}$) 114.1, C$_{cc}$) 124.0, C$_{bb}$) 129.1, C$_{ii}$) 130.0, C$_{ee}$) 130.3, C$_{jj}$) 158.6, C$_{kk}$) 168.6, 169.3, 170.5, 170.6, 171.3, 171.5, 172.4, 173.9, 204.9; IR (neat) 3337 (s), 2959 (s), 2870 (m), 1733 (s), 1645 (s), 1640 (s), 1543 (m), 1514 (m), 1454 (m), 1407 (m), 1368 (m), 1302 (w), 1248 (m), 1171 (m) cm$^{-1}$; HRMS m/z calculated for C$_{59}$H$_{91}$N$_7$O$_{15}$ (M+Na) 1160.6471, found 1160.6415.

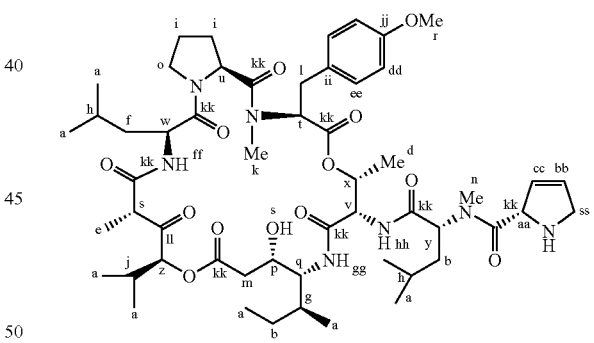

Cyclo[N—(N-3,4-dehydro-L-prolyl-N-methyl-D-leucyl)-O[[N-[(2S,3S,4S)-4[(3S,4R,5S)-4-amino-3-hydroxy-5-methyl-heptanoyl]oxy-3-oxo-2,5-dimethylhexanoyl]-L-leucyl]-L-prolyl-N,O-dimethyl-L-tyrosyl]-L-threonyl] (compound 59). Compound 58 (4 milligrams) was dissolved in HCl.dioxane (0.5 milliliter) and stirred at room temperature. When the reaction was completed, the solvent was removed in vacuo. Toluene was added twice, and the solution was concentrated. The residue was dried in vacuo overnight to afford the desired HCl salt in 98%. The HCl salt was dissolved in EtOAc, washed with saturated NaHCO$_3$, and the organic layer washed again with brine, dried over Na$_2$SO$_4$, and concentrated to afford the desired product (compound 59) in 75% yield. The following analytical data were obtained for compound 59: $R_f$ 0.20 (10% MeOH/CH$_2$Cl$_2$); $[\alpha]_D^{25}$ −242.3 (c=0.2, CHCl$_3$); $^1$H NMR (500 MHz, CDCl$_3$) δ H$_a$) 0.79-0.97 (m, 24H), H$_b$) 1.12-1.23 (m, 3H), H$_d$) 1.32-1.40 (d, 3H), H$_e$) 1.43 (d, 3H), H$_f$) 1.46-1.50 (m, 1H) and 1.61 (t, 1H), H$_g$) 1.68-1.73 (m, 1H), H$_h$) 1.74-1.79 (m, 1H), H$_i$ & H$_j$) 1.82-1.88 (m, 2H), 2.02-2.08 (m, 1H) and 2.11-2.17 (m, 3H), H$_k$) 2.25 (s, 3H), H$_l$) 2.51 (d, 2H), H$_m$) 3.18 and 3.39 (dd, 1H), H$_n$) 2.95 (s, 3H), H$_o$) 3.57-3.61 (m, 2H), H$_p$) 3.33 (d, 1H), H$_q$) 3.69-3.71 (m, 1H), H$_r$) 3.73 (s, 3H), H$_s$) 3.90-4.18 (m, 2H), H$_t$) 4.49 (q, 1H), H$_u$) 4.56 (dd, 1H), H$_v$) 4.65 (dd, 1H), H$_w$) 4.81 (t, 1H), H$_x$) 5.19 (m, 3H), H$_{bb}$ & H$_{aa}$) 5.73-5.75 (m, 3H), H$_{cc}$ & H$_z$) 6.01 (dd, 3H), H$_{dd}$) 6.85 (d, 2H), H$_{ee}$) 7.08 (d, 2H), H$_{ff}$) 7.20 (d, 1H), H$_{gg}$) 7.54 (d, 1H), H$_{hh}$) 7.78 (d, 1H); $^{13}$C NMR (125 MHz, CDCl$_3$) δ C$_a$) 11.7, 14.7, 15.2, 16.3, 16.9, 18.6, 20.1 and 20.9, C$_d$) 23.3, C$_e$) 23.7, C$_a$) 24.8 and 27.2, C$_i$) 24.9, 25.0 and 33.9, C$_f$) 27.9, C$_c$) 28.6, C$_g$) 31.2, C$_h$) 31.3, C$_j$) 33.9, C$_l$) 36.2, C$_m$) 38.7, C$_k$) 38.8, C$_n$) 41.3, C$_o$) 46.9, C$_q$) 49.46, C$_s$) 49.52, 53.0, and 67.9, C$_r$) 55.3, C$_v$) 55.4, C$_w$) 55.5, C$_u$) 57.2, C$_y$) 57.6, C$_t$) 63.9, C$_{aa}$) 65.9, C$_p$) 66.5, C$_x$) 70.4, C$_z$) 81.5, C$_{dd}$) 114.1, C$_{cc}$) 124.0, C$_{bb}$) 129.1, C$_{ii}$) 130.0, C$_{ee}$) 130.3, C$_{jj}$) 158.6, C$_{kk}$) 168.6, 169.3, 170.5, 171.3, 171.5, 172.4, 173.9, C$_{ll}$) 204.9; IR (neat) 3337 (s), 2958 (s), 2861 (m), 1734 (s), 1642 (s), 1638 (s), 1547 (m), 1514 (m), 1451 (m), 1385 (w), 1243 (w), 1166 (w) cm$^{-1}$; HRMS m/z calculated for C$_{54}$H$_{83}$N$_7$O$_{13}$ (M+H) 1038.6127, found 1038.6103.

The disclosure of every patent, patent application, and publication cited herein is hereby incorporated herein by reference in its entirety.

While this invention has been disclosed with reference to specific embodiments, other embodiments and variations of this invention can be devised by others skilled in the art without departing from the true spirit and scope of the invention. The appended claims include all such embodiments and equivalent variations.

What is claimed is:

1. A pharmaceutical composition comprising a tamandarin analog having the structure

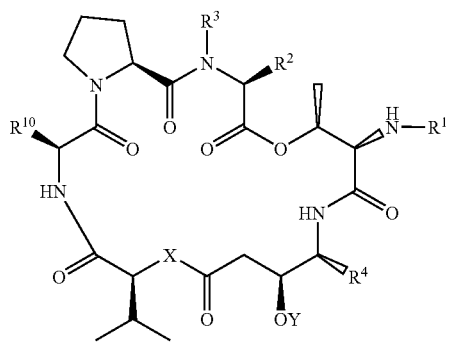

wherein:
i) R$^1$ is selected from the group consisting of
—(N-methyl)leucine-deoxo-proline,
—(N-methyl)leucine-deoxo-proline-lactate,
—(N-methyl)leucine-deoxo-proline-pyruvate,
—(N-methyl)leucine-deoxo-proline-lactate-(a first fluorophore),
—(N-methyl)leucine-deoxo-proline-lactate-glutamine-pyroglutamate,
—(N-methyl)leucine-deoxo-proline-lactate-glutamine-cyclopentanoate,
—(N-methyl)leucine-deoxo-proline-alanine-leucine-pyroglutamate,
—(N-methyl)leucine-deoxo-proline-(N-methyl-alanine)-leucine-pyroglutamate,
—(N-methyl)leucine-dehydro-proline,
—(N-methyl)leucine-dehydro-proline-lactate,
—(N-methyl)leucine-dehydro-proline-pyruvate,
—(N-methyl)leucine-dehydro-proline-lactate-(a first fluorophore),
—(N-methyl)leucine-dehydro-proline-lactate-glutamine-pyroglutamate,
—(N-methyl)leucine-dehydro-proline-lactate-glutamine-cyclopentanoate,
—(N-methyl)leucine-dehydro-proline-alanine-leucine-pyroglutamate and
—(N-methyl)leucine-dehydro-proline-(N-methyl-alanine)-leucine-pyroglutamate ii) R$^2$ and R$^3$ are one of
(a) R$^2$ is selected from the group consisting of an isoleucine side chain, a valine side chain, an alanine side chain, a norleucine side chain, a norvaline side chain, a leucine side chain, a histidine side chain, a tryptophan side chain, an arginine side chain, a lysine side chain, a second fluorophore, and a substituent having the structure

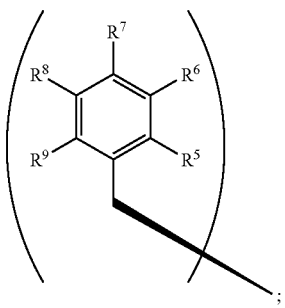

and R$^3$ is selected from the group consisting of —CH$_3$ and —H; or
(b) R$^2$ and R$^3$ form the structure

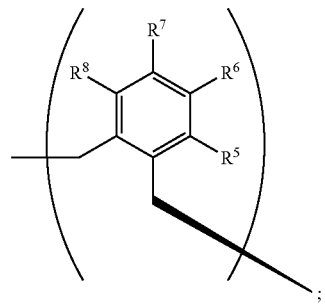

iii) each of R$^5$, R$^6$, R$^7$, R$^8$, and R$^9$, when present, is independently selected from the group consisting of —H, —OH, —OCH$_3$, —CO(C$_6$H$_5$), —Br, —I, —F, —Cl, —CH$_3$, and —C$_2$H$_5$;
iv) R$^4$ is selected from the group consisting of an isoleucine side chain and a valine side chain;
v) X is selected from the group consisting of —O— and —(NH)—;

vi) Y is selected from the group consisting of —H and a hydroxyl protecting group; and
vii) $R^{10}$ is selected from the group consisting of a leucine side chain and a lysine side chain; and
a pharmaceutically acceptable carrier.

2. The pharmaceutical composition of claim 1, wherein $R^1$ is selected from the group consisting of
—(N-methyl)leucine-deoxo-(S)proline,
—(N-methyl)leucine-deoxo-(S)proline-(S)lactate,
—(N-methyl)leucine-deoxo-(S)proline-pyruvate,
—(N-methyl)leucine-deoxo-(S)proline-(S)lactate-(a first fluorophore),
—(N-methyl)leucine-deoxo-(S)proline-(S)lactate-glutamine-pyroglutamate,
—(N-methyl)leucine-deoxo-(S)proline-(S)lactate-glutamine-cyclopentanoate,
—(N-methyl)leucine-deoxo-(S)proline-alanine-leucine-pyroglutamate,
—(N-methyl)leucine-deoxo-(S)proline-(N-methyl-alanine)-leucine-pyroglutamate,
—(N-methyl)leucine-dehydro-(S)proline,
—(N-methyl)leucine-dehydro-(S)proline-(S)lactate,
—(N-methyl)leucine-dehydro-(S)proline-pyruvate,
—(N-methyl)leucine-dehydro-(S)proline-(S)lactate-(a first fluorophore),
—(N-methyl)leucine-dehydro-(S)proline-(S)lactate-glutamine-pyroglutamate,
—(N-methyl)leucine-dehydro-(S)proline-(S)lactate-glutamine-cyclopentanoate,
—(N-methyl)leucine-dehydro-(S)proline-alanine-leucine-pyroglutamate and
—(N-methyl)leucine-dehydro-(S)proline-(N-methyl-alanine)-leucine-pyroglutamate.

3. The composition of claim 1, wherein $R^1$ is selected from the group consisting of
—(N-methyl)leucine-deoxo-(S)proline,
—(N-methyl)leucine-deoxo-(S)proline-(S)lactate,
—(N-methyl)leucine-deoxo-(S)proline-pyruvate,
—(N-methyl)leucine-deoxo-(S)proline-(S)lactate-(a first fluorophore),
—(N-methyl)leucine-deoxo-(S) proline-(S)lactate-(S)glutamine-(S)pyroglutamate,
—(N-methyl)leucine-deoxo-(S)proline-(S)lactate-(S)glutamine-(S)cyclopentanoate,
—(N-methyl)leucine-deoxo-(S)proline-(S)alanine-(S)leucine-(S)pyroglutamate,
—(N-methyl)leucine-deoxo-(S)proline-(N-methyl-(S)-alanine)-(S)leucine-(S)pyroglutamate,
—(N-methyl)leucine-dehydro-(S)proline,
—(N-methyl)leucine-dehydro-(S)proline-(S)lactate,
—(N-methyl)leucine-dehydro-(S)proline-pyruvate,
—(N-methyl)leucine-dehydro-(S)proline-(S)lactate-(a first fluorophore),
—(N-methyl)leucine-dehydro-(S)proline-(S)lactate-(S)glutamine-(S)pyroglutamate,
—(N-methyl)leucine-dehydro-(S)proline-(S)lactate-(S)glutamine-(S)cyclopentanoate,
—(N-methyl)leucine-dehydro-(S)proline-(S)alanine-(S)leucine-(S)pyroglutamate, and
—(N-methyl)leucine-dehydro-(S)proline-(N-methyl-(S)-alanine)-(S)leucine-(S)pyroglutamate.

4. The pharmaceutical composition of claim 1, wherein $R^2$ is

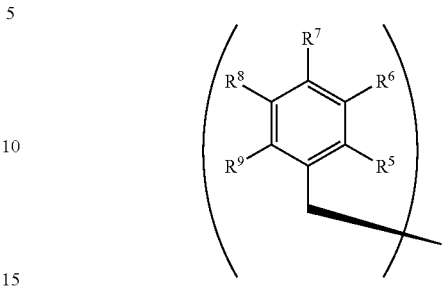

$R^3$ is methyl, $R^4$ is an isoleucine side chain, each of $R^5$, $R^6$, $R^8$, and $R^9$ is a hydride radical, $R^7$ is methoxy, $R^{10}$ is a leucine side chain, X is —O—, and Y is a hydride radical.

5. The pharmaceutical composition of claim 1, wherein the tamandarin analog is

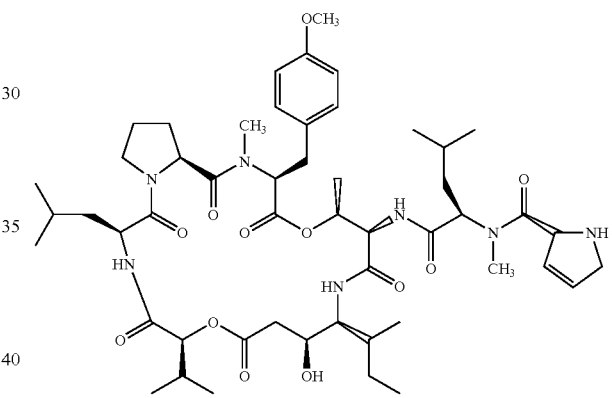

6. The pharmaceutical composition of claim 1, wherein $R^1$ is —(N-methyl)leucine-deoxo(S)proline-lactate.

7. The pharmaceutical composition of claim 1, wherein $R^4$ is a valine side chain, Y is —H, and X is —O—.

8. The pharmaceutical composition of claim 1, wherein Y is —H, and wherein $R^2$ has the structure

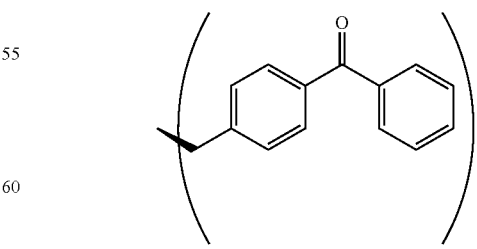

9. The pharmaceutical composition of claim 1, wherein $R^2$ is a lysine side chain and Y is —H.

10. The pharmaceutical composition of claim 1, wherein the tamandarin analog has the following structure

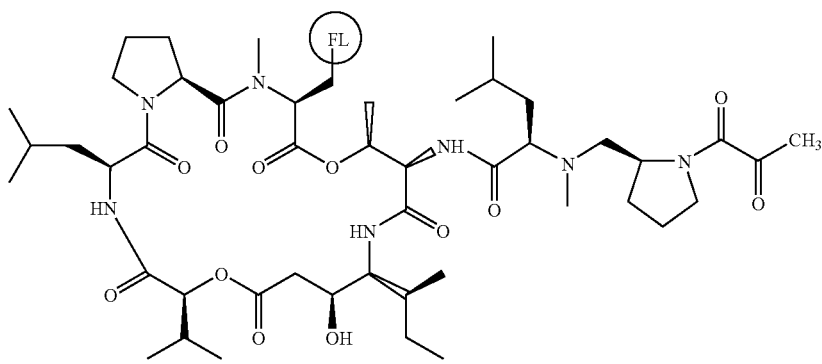

wherein FL is a fluorophore.

11. The pharmaceutical composition of claim 1, wherein X is —NH—.

12. The pharmaceutical composition of claim 1, wherein the tamandarin analog is present in about 1% to about 10% (w/w) in the form of a topically-administrable formulation.

13. The pharmaceutical composition of claim 1, wherein the tamandarin analog is:

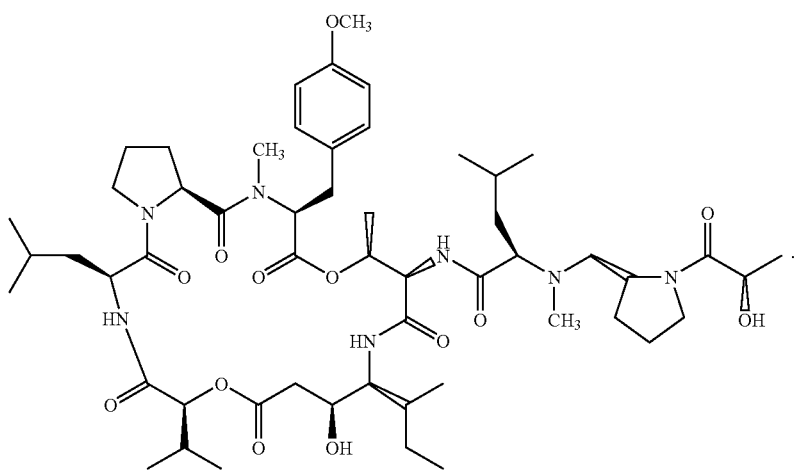

14. A pharmaceutical composition comprising a compound having a structure selected from the group consisting of

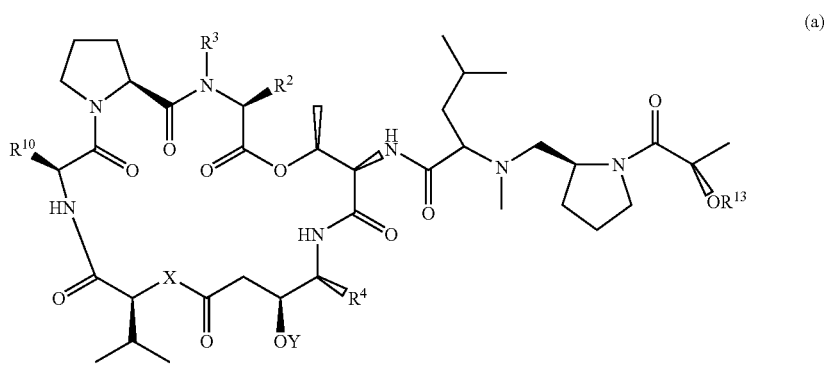

(a)

(b)

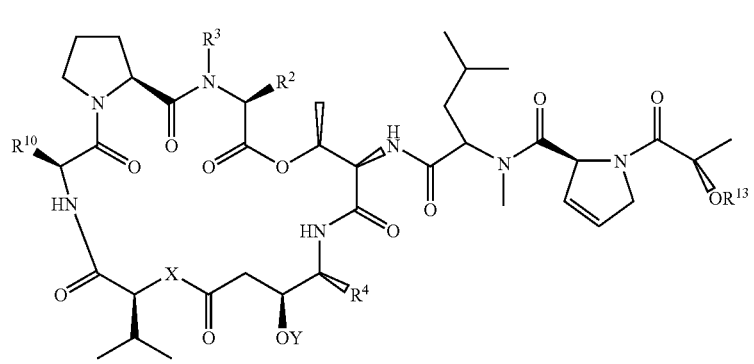

(c)

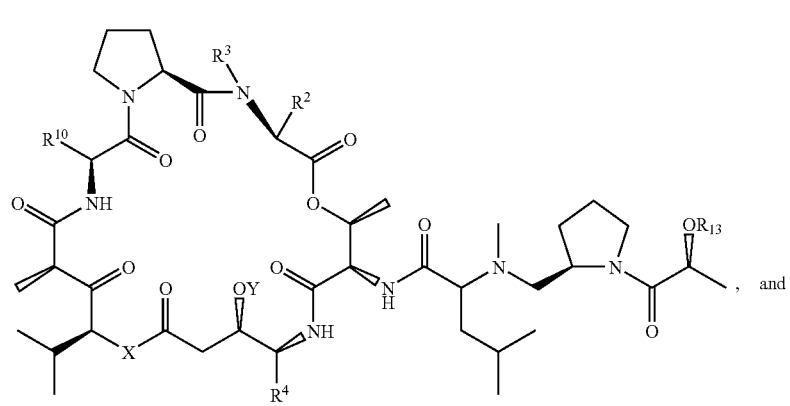
, and (d)

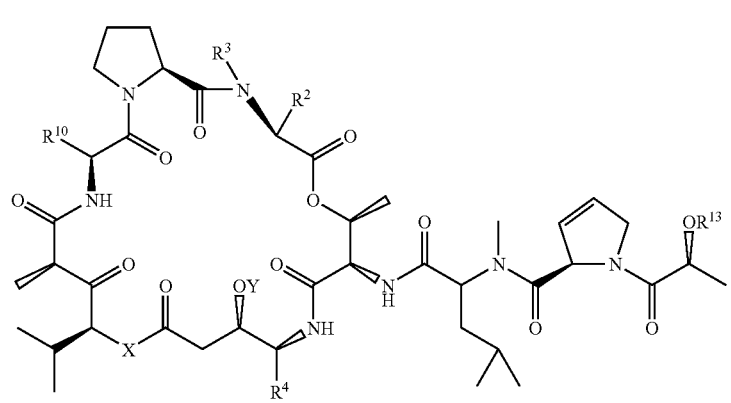

wherein:
i) $R^2$ and $R^3$ are one of
(a) $R^3$ is selected from the group consisting of —$CH_3$ and —H; and $R^2$ is selected from the group consisting of an isoleucine side chain, a valine side chain, an alanine side chain, a norleucine side chain, a norvaline side chain, a proline side chain, a leucine side chain, a histidine side chain, a tryptophan side chain, an arginine side chain, a lysine side chain, a second fluorophore, and a substituent having the structure

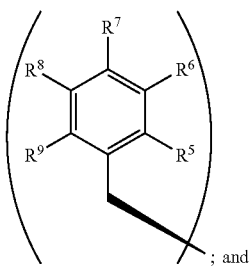

(b) R² and R³ together are a substituent having the structure

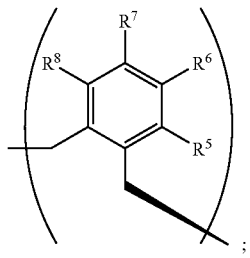

ii) each of R⁵, R⁶, R⁷, R⁸, and R⁹, when present, is independently selected from the group consisting of —H, —OH, —OCH₃, —CO(C₆H₅), —Br, —I, —F, —Cl, —CH₃, and —C₂H₅;

iii) R⁴ is selected from the group consisting of an isoleucine side chain and a valine side chain;

iv) X is selected from the group consisting of —O— and —NH—;

v) Y is selected from the group consisting of —H and a hydroxyl protecting group;

vi) R¹⁰ is selected from the group consisting of a leucine side chain and a lysine side chain; and vii) R¹³ is an enzyme-cleavable moiety that is cleavable by an enzyme selected from the group consisting of a carboxypeptidase, a beta-lactamase, a beta galactosidase, a penicillin V-amidase, a cytosine deaminase, a nitroreductase, an alkaline phosphatase, a beta-glucuronidase, and a catalytic antibody; and a pharmaceutically acceptable earner.

15. The pharmaceutical composition of claim 14, wherein R¹³ has the structure

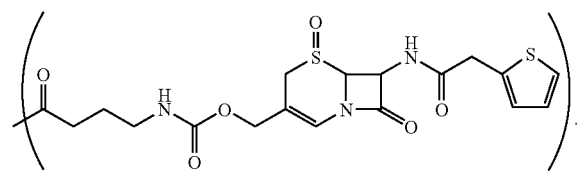

16. The pharmaceutical composition of claim 14, wherein R¹³ has the structure

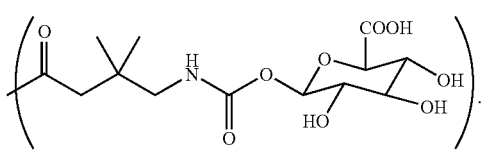

17. A pharmaceutical composition comprising a didemnin analog having the structure

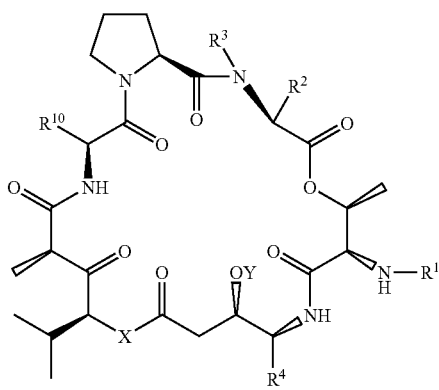

wherein:

i) R¹ is selected from the group consisting of
—(N-methyl)leucine-deoxo-proline,
—(N-methyl)leucine-deoxo-proline-lactate,
—(N-methyl)leucine-deoxo-proline-pyruvate,
—(N-methyl)leucine-deoxo-proline-lactate-(a first fluorophore),
—(N-methyl)leucine-deoxo-proline-lactate-glutamine-pyroglutamate,
—(N-methyl)leucine-deoxo-proline-lactate-glutamine-cyclopentanoate,
—-(N-methyl)leucine-deoxo-proline-alanine-leucine-pyroglutamate,
—-(N-methyl)leucine-deoxo-proline-(N-methyl-alanine)-leucine-pyroglutamate,
—(N-methyl)leucine-dehydro-proline-pyruvate,
—(N-methyl)leucine-dehydro-proline-lactate-(a first fluorophore),
—(N-methyl)leucine-dehydro-proline-lactate-glutamine-pyroglutamate,
—(N-methyl)leucine-dehydro-proline-lactate-glutamine-cyclopentanoate,
—(N-methyl)leucine-dehydro-proline-alanine-leucine-pyroglutamate, and
—(N-methyl)leucine-dehydro-proline-(N-methyl-alanine)-leucine-pyroglutamate;

ii) R² and R³ are one of
(a) R³ selected from the group consisting of —CH₃ and —H; and R² is selected from the group consisting of an isoleucine side chain, a valine side chain, an alanine side chain, a norleucine side chain, a norvaline side chain a leucine side chain, a histidine side chain, a tryptophan side chain, an arginine side chain, a lysine side chain, a second fluorophore, and a substituent having the structure

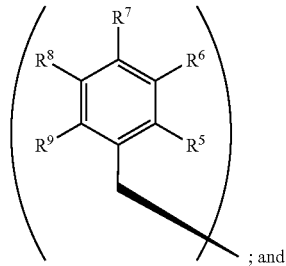

; and (b) $R^2$ and $R^3$ together are a substituent having the structure

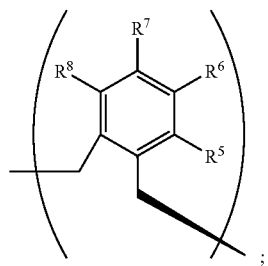

;

iii) each of $R^5$, $R^6$, $R^7$, $R^8$ and $R^9$, when present, is independently selected from the group consisting of —H, —OH, —OCH$_3$, —CO(C$_6$H$_5$), —Br, —I, —F, —Cl, —CH$_3$, and —C$_2$H$_5$;
iv) $R^4$ is selected from the group consisting of an isoleucine side chain and a valine side chain;
v) X is selected from the group consisting of —O— and —NH—;
vi) Y is selected from the group consisting of —H and a hydroxyl protecting group; and
vii) $R^{10}$ is selected from the group consisting of a leucine side chain and a lysine side chain; and
a pharmaceutically acceptable carrier.

18. The pharmaceutical composition of claim 17, wherein $R^1$ is selected from the group consisting of
—(N-methyl)leucine-deoxo-(S)proline,
—(N-methyl)leucine-deoxo-(S)proline-(S)lactate,
—(N-methyl)leucine-deoxo-(S)proline-pyruvate,
—(N-methyl)leucine-deoxo-(S)proline-(S)lactate-(a first fluorophore),
—(N-methyl)leucine-deoxo-(S)proline-(S)lactate-glutamine-pyroglutamate,
—(N-methyl)leucine-deoxo-(S)proline-(S)lactate-glutamine-cyclopentanoate,
—(N-methyl)leucine-deoxo-(S)proline-alanine-leucine-pyroglutamate,
—(N-methyl)leucine-deoxo-(S)proline-(N-methyl-alanine)-leucine-pyroglutamate,
—(N-methyl)leucine-dehydro-(S)proline-pyruvate,
—(N-methyl)leucine-dehydro-(S)proline-(S)lactate-(a first fluorophore),
—(N-methyl)leucine-dehydro-(S)proline-(S)lactate-glutamine-pyroglutamate,
—(N-methyl)leucine-dehydro-(S)proline-(S)lactate-glutamine-cyclopentanoate,
—(N-methyl)leucine-dehydro-(S)proline-alanine-leucine-pyroglutamate, and
—(N-methyl)leucine-dehydro-(S)proline-(N-methyl-alanine)-leucine-pyroglutamate.

19. The pharmaceutical composition of claim 17, wherein $R^1$ is selected from the group consisting of
—(N-methyl)leucine-deoxo-(S)proline,
—(N-methyl)leucine-deoxo-(S)proline-(S)lactate,
—(N-methyl)leucine-deoxo-(S)proline-pyruvate,
—(N-methyl)leucine-deoxo-(S)proline-(S)lactate-(a first fluorophore),
—(N-methyl)leucine-deoxo-(S)proline-(S)lactate-(S)glutamine-(S)pyroglutamate,
—(N-methyl)leucine-deoxo-(S)proline-(S)lactate-(S)glutamine-(S)cyclopentanoate,
—(N-methyl)leucine-deoxo-(S)proline-(S)alanine-(S)leucine-(S)pyroglutamate,
—(N-methyl)leucine-deoxo-(S)proline-(N-methyl-(S)alanine)-(S)leucine-(S)pyroglutamate,
—(N-methyl)leucine-dehydro-(S)proline-pyruvate,
—(N-methyl)leucine-dehydro-(S)proline-(S)lactate-(a first fluorophore),
—(N-methyl)leucine-dehydro-(S)proline-(S)lactate-(S)glutamine-(S)pyroglutamate,
—(N-methyl)leucine-dehydro-(S)proline-(S)lactate-(S)glutamine-(S)cyclopentanoate,
(N-methyl)leucine-dehydro-(S)proline-(S)alanine-(S)leucine-(S)pyroglutamate, and
—-(N-methyl)leucine-dehydro-(S)proline-(N-methyl-(S)alanine)-(S)leucine-(S)pyroglutamate.

20. The pharmaceutical composition of claim 17, wherein $R^2$ is

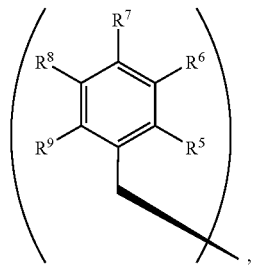

, $R^3$ is methyl, $R^4$ is an isoleucine side chain, each of $R^5$, $R^6$, $R^8$, and $R^9$ is —H, $R^7$ is methoxy, $R^{10}$ is a leucine side chain, X is —O—, and Y is —H.

21. The pharmaceutical composition of claim 17, wherein the didemnin analog is

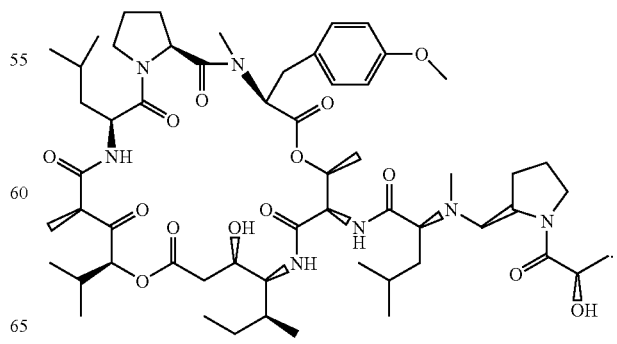

22. The pharmaceutical composition of claim 17, wherein $R^1$ is —(N-methyl)leucine-deoxo-(S)proline-lactate.

23. The pharmaceutical composition of claim 17, wherein Y is —H, and wherein $R^2$ has the structure

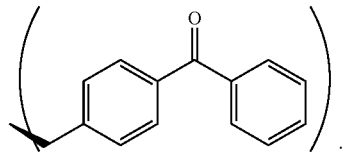

24. The pharmaceutical composition of claim 17, wherein $R^2$ is a lysine side chain and Y is —H.

25. The pharmaceutical composition of claim 17, wherein X is —NH—.

26. The pharmaceutical composition of claim 17, wherein the didemnin analog is present in about 1% to about 10% (w/w) in the form of a topically-administrable formulation.

27. A compound of formula

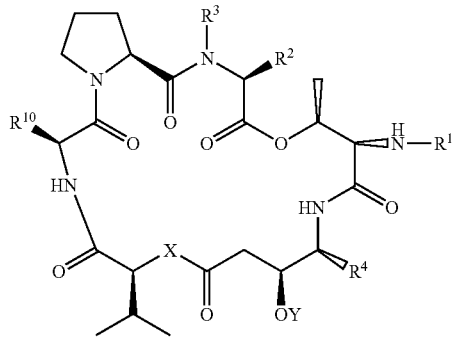

wherein:

i) $R^1$ is selected from the group consisting of
- —(N-methyl)leucine-deoxo-(S)proline,
- —(N-methyl)leucine-deoxo-(S)proline-(S)lactate,
- —(N-methyl)leucine-deoxo-(S)proline-pyruvate,
- —(N-methyl)leucine-deoxo-(S)proline-(S)lactate-(a first fluorophore),
- —(N-methyl)leucine-deoxo-(S) proline-(S)lactate-(S)glutamine-(S)pyroglutamate,
- —(N-methyl)leucine-deoxo-(S)proline-(S)lactate-(S)glutamine-(S)cyclopentanoate,
- —(N-methyl)leucine-deoxo-(S)proline-(S)alanine-(S)leucine-(S)pyroglutamate,
- —(N-methyl)leucine-deoxo-(S)proline-(N-methyl-(S)-alanine)-(S)leucine-(S)pyroglutamate
- —(N-methyl)leucine-dehydro-(S)proline,
- —(N-methyl)leucine-dehydro-(S)proline-(S)lactate,
- —(N-methyl)leucine-dehydro-(S)proline-pyruvate,
- —(N-methyl)leucine-dehydro-(S)proline-(S)lactate-(a first fluorophore),
- —(N-methyl)leucine-dehydro-(S)proline-(S)lactate-(S)glutamine-(S)pyroglutamate,
- —(N-methyl)leucine-dehydro-(S)proline-(S)lactate-(S)glutamine-(S)cyclopentanoate,
- —(N-methyl)leucine-dehydro-(S)proline-(S)alanine-(S)leucine-(S)pyroglutamate, and
- —(N-methyl)leucine-dehydro-(S)proline-(N-methyl-(S)-alanine)-(S)leucine-(S)pyroglutamate;

ii) $R^2$ and $R^3$ are one of (a) $R^2$ is selected from the group consisting of an isoleucine side chain, a valine side chain, an alanine side chain, a norleucine side chain, a norvaline side chain, a leucine side chain, a histidine side chain, a tryptophan side chain, an arginine side chain, a lysine side chain, a second fluorophore, and a substituent having the structure

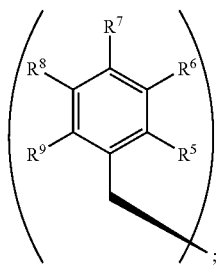

and $R^3$ is selected from the group consisting of —$CH_3$ and —H; or (b) $R^2$ and $R^3$ form the structure

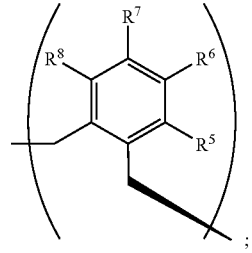

iii) each of $R^5$, $R^6$, $R^7$, $R^8$, and $R^9$, when present, is independently selected from the group consisting of —H, —OH, —$OCH_3$, —$CO(C_6H_5)$, —Br, —I, —F, —Cl, —$CH_3$, and iv) $R^4$ is selected from the group consisting of an isoleucine side chain and a valine side chain;

v) X is selected from the group consisting of —O— and —(NH)—;

vi) Y is selected from the group consisting of —H and a hydroxyl protecting group; and vii) $R^{10}$ is selected from the group consisting of a leucine side chain and a lysine side chain.

* * * * *